(12) United States Patent
Zamora et al.

(10) Patent No.: US 7,671,012 B2
(45) Date of Patent: Mar. 2, 2010

(54) FORMULATIONS AND METHODS FOR DELIVERY OF GROWTH FACTOR ANALOGS

(75) Inventors: Paul O. Zamora, Gaithersburg, MD (US); Sarah Campion, Danville, CA (US)

(73) Assignee: BioSurface Engineering Technologies, Inc., Rockville, MD (US)

(*) Notice: Subject to any disclaimer, the term of this patent is extended or adjusted under 35 U.S.C. 154(b) by 766 days.

(21) Appl. No.: 11/361,090

(22) Filed: Feb. 23, 2006

(65) Prior Publication Data

US 2006/0205652 A1    Sep. 14, 2006

Related U.S. Application Data

(63) Continuation-in-part of application No. 11/359,173, filed on Feb. 21, 2006, and a continuation-in-part of application No. 11/167,636, filed on Jun. 27, 2005, which is a continuation-in-part of application No. 11/055,428, filed on Feb. 10, 2005, now Pat. No. 7,528,105.

(60) Provisional application No. 60/656,714, filed on Feb. 25, 2005, provisional application No. 60/656,713, filed on Feb. 25, 2005, provisional application No. 60/656,174, filed on Feb. 25, 2005, provisional application No. 60/543,616, filed on Feb. 10, 2004, provisional application No. 60/655,570, filed on Feb. 22, 2005.

(51) Int. Cl.
*A61K 38/18* (2006.01)
*A61K 38/10* (2006.01)

(52) U.S. Cl. .............. 514/2; 514/14; 514/15; 530/326; 530/328

(58) Field of Classification Search .......... None
See application file for complete search history.

(56) References Cited

U.S. PATENT DOCUMENTS

| | | | |
|---|---|---|---|
| 4,172,128 A | 10/1979 | Thiele et al. |
| 4,563,350 A | 1/1986 | Nathan et al. |
| 5,563,046 A | 10/1996 | Mascarenhas et al. |
| 5,608,035 A | 3/1997 | Yanofsky et al. |
| 5,635,597 A | 6/1997 | Barrett et al. |
| 5,643,873 A | 7/1997 | Barrett et al. |
| 5,648,458 A | 7/1997 | Cwirla et al. |
| 5,654,276 A | 8/1997 | Barrett et al. |
| 5,668,110 A | 9/1997 | Barrett et al. |
| 5,674,977 A | 10/1997 | Gariepy |
| 5,679,637 A | 10/1997 | Lappi et al. |
| 5,679,673 A | 10/1997 | Bowen et al. |
| 5,684,136 A | 11/1997 | Godowski |
| 5,728,802 A | 3/1998 | Barrett et al. |
| 5,759,515 A | 6/1998 | Rhodes et al. |
| 5,767,234 A | 6/1998 | Yanofsky et al. |
| 5,770,704 A | 6/1998 | Godowski |
| 5,773,569 A | 6/1998 | Wrighton et al. |
| 5,786,322 A | 7/1998 | Barrett et al. |
| 5,786,331 A | 7/1998 | Barrett et al. |
| 5,789,182 A | 8/1998 | Yayon et al. |
| 5,830,851 A | 11/1998 | Wrighton et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,932,462 A | 8/1999 | Harris et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. |
| 6,011,002 A | 1/2000 | Pastan et al. |
| 6,030,812 A | 2/2000 | Bauer et al. |
| 6,051,648 A | 4/2000 | Rhee et al. |
| 6,121,236 A | 9/2000 | Ben-Sasson |
| 6,168,784 B1 | 1/2001 | Offord et al. |
| 6,174,530 B1 | 1/2001 | Rose et al. |
| 6,174,721 B1 | 1/2001 | Innis |
| 6,214,795 B1 | 4/2001 | Benjamin et al. |
| 6,217,873 B1 | 4/2001 | Rose et al. |
| 6,235,716 B1 | 5/2001 | Ben-Sasson |
| 6,251,864 B1 | 6/2001 | Dower et al. |
| 6,284,503 B1 | 9/2001 | Caldwell et al. |
| 6,294,359 B1 | 9/2001 | Fiddes et al. |
| 6,323,323 B1 | 11/2001 | Sledziewski et al. |
| 6,326,468 B1 | 12/2001 | Canne et al. |
| 6,342,591 B1 | 1/2002 | Zamora et al. |
| 6,350,731 B1 | 2/2002 | Jehanli et al. |
| 6,377,349 B1 | 4/2002 | Fercher |
| 6,451,543 B1 | 9/2002 | Kochendoerfer et al. |
| 2003/0224996 A1 | 12/2003 | Opperman et al. |

(Continued)

FOREIGN PATENT DOCUMENTS

WO    WO-00/18921    4/2000

(Continued)

OTHER PUBLICATIONS

Ahmed, Asif et al., "Role of VEFGF Receptor-1 (Fit-1) in Mediating Calcium-Dependent Nitric Oxide Release and Limiting DNA Synthesis in Human Trophoblast Cells", *Lab Invet*, vol. 76(6) 1997, 779-791.

(Continued)

*Primary Examiner*—Anish Gupta
(74) *Attorney, Agent, or Firm*—Janeen Vilven; Peacock Myers, P.C.

(57) ABSTRACT

Formulations, kits and methods for bone or cartilage repair, including treatment of osteogenic defects, including formulations of synthetic heparin-binding growth factor analogs, non-ionic polymers, gelling agents and calcium-containing agents.

2 Claims, 5 Drawing Sheets

U.S. PATENT DOCUMENTS

2004/0087505 A1    5/2004    Pena et al.
2004/0151764 A1*   8/2004    Zamora .................... 424/445

FOREIGN PATENT DOCUMENTS

| WO | WO-00/64481 | 11/2000 |
|----|-------------|---------|
| WO | WO02/04015 | 1/2002 |
| WO | WO0210221 | 2/2002 |
| WO | WO02/19963 | 3/2002 |
| WO | WO-02/20033 | 3/2002 |
| WO | WO-02/062823 | 8/2002 |

OTHER PUBLICATIONS

Andrades, Jose A. et al., "A Recombinant Human TGF-B1 Fusion Protein with Collagen-Binding Domain Promostes Migration, Growth, and Differentiation of Bone Marrow Mesenchymal Cells", *Experimental Cell Research* 1999, 485-498.

Ballinger, Marcus D. et al., "Semirational design of a potent, artificial agonist of fibroblast growth factor receptors", *Nature Biotechnology* 1999, 1199-1204.

Binetruy-Tournaire, Roselyne et al., "Identification of a Peptide Blocking Vascular Endothelial Growth Factor (VEGF)-mediated Angiogenesis", *The EMBO Journal*, vol. 19, No. 7 2000, 1525-1533.

Bork, Peer et al., "Go Hunting in Sequence Databases But Watch Out For Traps", *TIG* Oct. 1996, 425-427.

Bork, Peer et al., "Powers and Pitfalls In Sequence Analysis: the 70% Hurdle", *Genome Research* 2000, 398-400.

Brennand, David M. et al., "Identification of a Cyclic Peptide Inhibitor of Platelet-Derived Growth Factor-BB Receptor-Binding and Mitogen-lnduced DNA Synthesis in Human Fibroblasts", *FEBS Letters*, 413 1997, 70-74.

Brenner, Steve et al., "Errors in Genome Annotation", *Trends in Genetics* Apr. 1999, 132-133.

Carmeliet, Peter et al., "Growing Better Blood Vessels", *Nature Biotechnology* 2001, 1019-1020.

Dawson, Philip E. et al., "Synthesis of Native Proteins by Chemical Ligation", *Annu. Rev. Biochem*, 2000, 69 2000, 923-960.

Dikov, Michael M. et al., "A Functional Fibroblast Growth Factor-1 Immunoglobulin Fusion Protein", *The Journal of Biological Chemistry* 1998, 15811-15817.

Doerks, Tobias et al., "Protein annotation: detective work for function prediction", *Trends in Genetics* Jun. 1998, 248-250.

Engstrom, Ulla et al., "Identification of a Peptide Antagonist for Platelet-Derived Growth Factor", *The Journal of Biological Chemistry*, vol. 273, No. 25 1998, 15811-15817.

Eom, Khee D. et al., "Tandem Ligation of Multipartite Peptides with Cell-Permeable Activity", *J. Am. Chem. Soc.*, 2003,125 2003, 73-83.

Gay, Cyril G. et al., "Interleukin 1 regulated heparin-binding growth factor 2 gene expression in vascular smooth muscle cells", *Proc. Natl. Acad. Sci. USA*, vol. 88 Jan. 1991, 296-300.

Hasan, Maemunah et al., "IL-12 is a Heparin-Binding Cytokine", *The Journal of Immunology* 1999, 1064-1070.

Hoke, David E. et al., "A heparin binding synthetic peptide from human HIP/RPL29 fails to specifically differentiate between anticoagulantly active and inactive species of heparin", *Journal of Negative Results in BioMedicine 2:1* 2003.

Kochendoefer, Gerd et al., "Design and Chemical Synthesis of Homogenous Polymer-Modified Erythropotesis Protein", *Science*, vol. 299 Feb. 7, 2003.

Ngo, Thomas et al., "Computational Complexity; Protein Structure Prediction, and the Levinthal Paradox", *The Protein Foling Problem and Terminary Structure Prediction* 1994.

Ostman, Arne et al., "Identification of Three Amino Acids in the Platelet-Derived Growth Factor (PDGF) B-chain that are Important for Binding to the PDGF B-Receptor", *The Journal of Biological Chemistry*, vol. 266, No. 16, Issue of Jun. 5, 1991 10073-10077.

Paris, Francois et al., "Endothelial Apoptosis as the Primary Lesion Initiating Intestinal Radiation Damage in Mice", *Science* 2001, 293-297.

Pellegrini, Luca et al., "Role of heparan sulfate in fibroblast growth factor signaling a structural view", *Structural Biology* 2001, 629-634.

Ray, Jasohara et al., "A 10-amino acid sequence of fibroblast growth factor 2 is sufficient for its mitogenic activity on neural progenitor cells", *Proc. Natl. Acad. Sci. USA* 1997, 7047-7052.

Richardson, Thomas P. et al., "Polymeric system for dual growth factor delivery", *Nature Biotechnology* 2001, 293-297.

Rusnati, Marco et al., "avB3 Integrin Mediates the Cell-adhesive Capacity and Biological Activity of Basic Fibroblast Growth Factor (FGF-2) in Cultured Endothelial Cells", *Molecular Biology of the Cell* 1997, 2449-2461.

Shen, Wei-Chiang et al., "Poly(I-lysine) has different membrane transport and drug-carrier properties when complexed with heparin", *Proc Natl Acad Sci USA* Dec. 1981, 7589-93.

Skolnick, Jeffrey et al., "From genes to protein structure and function: novel applications of computational approaches in the genomic era", *TIBTECH* Jan. 2000, 34-49.

Smith, Temple F. et al., "The challenges of genome sequence annotation of "The devil is in the details"", *Nature Biotechnology*, vol. 15 Nov. 1997, 1222-1223.

Sood, R. et al., "MDS1/EVI1 enhances TGF-B1 signaling and strengthens its growth-inhibitory effect, but the leukemia-associated fusion protein AML1/MDS1/EVI1, product of the t(3:21), abrogates growth-inhibition in response to TGF-B1", *Leukemia* 1999, 348-357.

Takizaw, Takuma et al., "Directly Linked Soluble IL-6 Receptor-IL-6 Fusion Protein Induces Astrocyte Differentiation from Neuroepithelial Cells Via Activation of STAT3", *Cytokine* 2001, 272-279.

Tanaka, H. et al., "Involvement of bone morphogenic protein-2 (BMP-2) in the pathological ossification process of the spinal ligament", *Rheumatology 2001*;40 May 9, 2001, 1163-1168.

Verrecchio, Angela et al., "Design of Peptides with High Affinities for Heparin and Endothelial Cell Proteoglycans", *The Journal of Biological Chemistry*, vol. 275, No. 11 Mar. 17, 2000, 7701-7707.

Wells, James A. et al., "Additivity of Mutational Effects in Proteins", *American Chemical Society*, vol. 29, No. 37 Sep. 18, 1990, 8509-8516.

Yoneda, Atsuko et al., "Engineering of an FGF-proteoglycan fusion protein with heparin-independent, mitogenic activity", *Nature Biotechnology* vol. 18 Jun. 2000, 641-644.

\* cited by examiner

SEQUENCE LISTING

```
<160> NUMBER OF SEQ ID NOS: 93

<210> SEQ ID NO 1
<211> LENGTH: 7
<212> TYPE: PRT
<213> ORGANISM: Artificial
<220> FEATURE:
<223> OTHER INFORMATION: Heparin binding motif
<220> FEATURE:
<221> NAME/KEY: misc_feature
<222> LOCATION: (1)..(3)
<223> OTHER INFORMATION: lysine or arginine
<220> FEATURE:
<221> NAME/KEY: misc_feature
<222> LOCATION: (4)..(5)
<223> OTHER INFORMATION: any natural or non-natural amino acid
<220> FEATURE:
<221> NAME/KEY: misc_feature
<222> LOCATION: (6)..(6)
<223> OTHER INFORMATION: lysine or arginine
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Xaa Xaa Xaa Xaa Xaa Xaa Xaa
1               5
```

-continued

<210> SEQ ID NO 2
<211> LENGTH: 10
<212> TYPE: PRT
<213> ORGANISM: Artificial
<220> FEATURE:
<223> OTHER INFORMATION: Heparin binding motif

<400> SEQUENCE: 2

```
Arg Lys Arg Lys Leu Glu Arg Ile Ala Arg
1               5                   10
```

<210> SEQ ID NO 3
<211> LENGTH: 10
<212> TYPE: PRT
<213> ORGANISM: Artificial
<220> FEATURE:
<223> OTHER INFORMATION: Heparin binding motif

<400> SEQUENCE: 3

```
Arg Lys Arg Lys Leu Gly Arg Ile Ala Arg
1               5                   10
```

<210> SEQ ID NO 4
<211> LENGTH: 10
<212> TYPE: PRT
<213> ORGANISM: Artificial
<220> FEATURE:
<223> OTHER INFORMATION: Heparin binding motif

<400> SEQUENCE: 4

```
Arg Lys Arg Lys Leu Trp Arg Ala Arg Ala
1               5                   10
```

<210> SEQ ID NO 5
<211> LENGTH: 9
<212> TYPE: PRT
<213> ORGANISM: Artificial
<220> FEATURE:
<223> OTHER INFORMATION: Heparin binding motif

<400> SEQUENCE: 5

```
Arg Lys Arg Leu Asp Arg Ile Ala Arg
1               5
```

<210> SEQ ID NO 6
<211> LENGTH: 11
<212> TYPE: PRT
<213> ORGANISM: Artificial
<220> FEATURE:
<223> OTHER INFORMATION: Heparin binding motif

<400> SEQUENCE: 6

```
Arg Lys Arg Lys Leu Glu Arg Ile Ala Arg Cys
1               5                   10
```

<210> SEQ ID NO 7
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 7

```
Tyr Arg Ser Arg Lys Tyr Ser Ser Trp Tyr Val Ala Leu Lys Arg
1               5                   10                  15
```

-continued

```
<210> SEQ ID NO 8
<211> LENGTH: 28
<212> TYPE: PRT
<213> ORGANISM: Artificial
<220> FEATURE:
<223> OTHER INFORMATION: Synthetic FGF analog

<400> SEQUENCE: 8

Asn Arg Phe His Ser Trp Asp Cys Ile Lys Thr Trp Ala Ser Asp Thr
1               5                   10                  15

Phe Val Leu Val Cys Tyr Asp Asp Gly Ser Glu Ala
            20                  25

<210> SEQ ID NO 9
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 9

His Ile Lys Leu Gln Leu Gln Ala Glu Glu Arg Gly Val Val Ser
1               5                   10                  15

<210> SEQ ID NO 10
<211> LENGTH: 17
<212> TYPE: PRT
<213> ORGANISM: Artificial
<220> FEATURE:
<223> OTHER INFORMATION: Synthetic FGF-1 analog

<400> SEQUENCE: 10

Tyr Ile Ser Lys Lys His Ala Glu Lys Asn Trp Phe Val Gly Leu Lys
1               5                   10                  15

Lys

<210> SEQ ID NO 11
<211> LENGTH: 15
<212> TYPE: PRT
<213> ORGANISM: Artificial
<220> FEATURE:
<223> OTHER INFORMATION: Synthetic FGF-1 analog

<400> SEQUENCE: 11

His Ile Gln Leu Gln Leu Ser Ala Glu Ser Val Gly Glu Val Tyr
1               5                   10                  15

<210> SEQ ID NO 12
<211> LENGTH: 20
<212> TYPE: PRT
<213> ORGANISM: Artificial
<220> FEATURE:
<223> OTHER INFORMATION: Synthetic FGF-7 analog

<400> SEQUENCE: 12

Tyr Ala Ser Ala Lys Trp Thr His Asn Gly Gly Glu Met Phe Val Ala
1               5                   10                  15

Leu Asn Gln Lys
            20

<210> SEQ ID NO 13
<211> LENGTH: 15
<212> TYPE: PRT
<213> ORGANISM: Artificial
<220> FEATURE:
```

<223> OTHER INFORMATION: Synthetic FGF-7 analog

<400> SEQUENCE: 13

Tyr Asn Ile Met Glu Ile Arg Thr Val Ala Val Gly Ile Val Ala
1               5                   10                  15

<210> SEQ ID NO 14
<211> LENGTH: 20
<212> TYPE: PRT
<213> ORGANISM: Artificial
<220> FEATURE:
<223> OTHER INFORMATION: Synthetic FGF-10 analog

<400> SEQUENCE: 14

Tyr Ala Ser Phe Asn Trp Gln His Asn Gly Arg Gln Met Tyr Val Ala
1               5                   10                  15

Leu Asn Gln Lys
            20

<210> SEQ ID NO 15
<211> LENGTH: 19
<212> TYPE: PRT
<213> ORGANISM: Artificial
<220> FEATURE:
<223> OTHER INFORMATION: Synthetic FGF-22 analog

<400> SEQUENCE: 15

Tyr Ala Ser Gln Arg Trp Arg Arg Arg Gly Gln Pro Asn Leu Ala Leu
1               5                   10                  15

Asp Arg Arg

<210> SEQ ID NO 16
<211> LENGTH: 21
<212> TYPE: PRT
<213> ORGANISM: Artificial
<220> FEATURE:
<223> OTHER INFORMATION: Synthetic FGF-9 analog

<400> SEQUENCE: 16

Tyr Ser Ser Asn Leu Tyr Lys His Val Asp Thr Gly Arg Arg Tyr Tyr
1               5                   10                  15

Val Ala Leu Asn Lys
            20

<210> SEQ ID NO 17
<211> LENGTH: 20
<212> TYPE: PRT
<213> ORGANISM: Artificial
<220> FEATURE:
<223> OTHER INFORMATION: Synthetic FGF-16 analog

<400> SEQUENCE: 17

Tyr Ala Ser Thr Leu Tyr Lys His Ser Asp Ser Glu Arg Gln Tyr Val
1               5                   10                  15

Ala Leu Asn Lys
            20

<210> SEQ ID NO 18
<211> LENGTH: 20
<212> TYPE: PRT
<213> ORGANISM: Artificial
<220> FEATURE:
<223> OTHER INFORMATION: Synthetic FGF-20 analog

<400> SEQUENCE: 18

Tyr Ser Ser Asn Ile Tyr Lys His Gly Asp Thr Gly Arg Arg Phe Val
1               5                   10                  15

Ala Leu Asn Lys
            20

<210> SEQ ID NO 19
<211> LENGTH: 16
<212> TYPE: PRT
<213> ORGANISM: Artificial
<220> FEATURE:
<223> OTHER INFORMATION: Synthetic FGF-4 analog

<400> SEQUENCE: 19

Tyr Glu Ser Tyr Lys Tyr Pro Gly Met Phe Ile Ala Leu Ser Lys Asn
1               5                   10                  15

<210> SEQ ID NO 20
<211> LENGTH: 17
<212> TYPE: PRT
<213> ORGANISM: Artificial
<220> FEATURE:
<223> OTHER INFORMATION: Synthetic FGF-6 analog

<400> SEQUENCE: 20

Tyr Glu Ser Asp Leu Tyr Gln Gly Thr Tyr Ile Leu Ser Lys Tyr Gly
1               5                   10                  15

Arg

<210> SEQ ID NO 21
<211> LENGTH: 20
<212> TYPE: PRT
<213> ORGANISM: Artificial
<220> FEATURE:
<223> OTHER INFORMATION: Synthetic FGF-12 analog

<400> SEQUENCE: 21

Tyr Ser Ser Thr Leu Tyr Arg Gln Gln Glu Ser Gly Arg Ala Trp Phe
1               5                   10                  15

Leu Gly Asn Lys
            20

<210> SEQ ID NO 22
<211> LENGTH: 21
<212> TYPE: PRT
<213> ORGANISM: Artificial
<220> FEATURE:
<223> OTHER INFORMATION: Synthetic FGF-14 analog

<400> SEQUENCE: 22

Tyr Ser Ser Met Leu Tyr Arg Gln Gln Glu Ser Gly Arg Ala Trp Phe
1               5                   10                  15

Leu Gly Leu Asn Lys
            20

<210> SEQ ID NO 23
<211> LENGTH: 21
<212> TYPE: PRT
<213> ORGANISM: Artificial
<220> FEATURE:
<223> OTHER INFORMATION: Synthetic FGF-13 analog

<400> SEQUENCE: 23

Tyr Ser Ser Met Ile Tyr Arg Gln Gln Gln Ser Gly Arg Gly Trp Tyr
1               5                   10                  15

Leu Gly Leu Asn Lys
            20

<210> SEQ ID NO 24
<211> LENGTH: 19
<212> TYPE: PRT
<213> ORGANISM: Artificial
<220> FEATURE:
<223> OTHER INFORMATION: Synthetic FGF-11 analog

<400> SEQUENCE: 24

Tyr Ala Ser Ala Leu Tyr Arg Gln Arg Arg Ser Gly Arg Ala Trp Tyr
1               5                   10                  15
Leu Asp Lys

<210> SEQ ID NO 25
<211> LENGTH: 10
<212> TYPE: PRT
<213> ORGANISM: Artificial
<220> FEATURE:
<223> OTHER INFORMATION: Synthetic FGF-1 analog

<400> SEQUENCE: 25

Ser Asn Gly Gly His Phe Leu Arg Ile Leu
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic FGF-2 analog

<400> SEQUENCE: 26

Lys Asn Gly Gly Phe Phe Leu Arg Ile His
1               5                   10

<210> SEQ ID NO 27
<211> LENGTH: 9
<212> TYPE: PRT
<213> ORGANISM: Artificial
<220> FEATURE:
<223> OTHER INFORMATION: Synthetic FGF-7 analog

<400> SEQUENCE: 27

Arg Thr Gln Trp Tyr Leu Arg Ile Asp
1               5

<210> SEQ ID NO 28
<211> LENGTH: 9
<212> TYPE: PRT
<213> ORGANISM: Artificial
<220> FEATURE:
<223> OTHER INFORMATION: Synthetic FGF-10 analog

<400> SEQUENCE: 28

Phe Thr Lys Tyr Phe Leu Lys Ile Glu
1               5

<210> SEQ ID NO 29
<211> LENGTH: 9
<212> TYPE: PRT
<213> ORGANISM: Artificial
<220> FEATURE:
<223> OTHER INFORMATION: Synthetic FGF-22 analog -continued

```
<400> SEQUENCE: 29

Ser Thr His Phe Phe Leu Arg Val Asp
1               5

<210> SEQ ID NO 30
<211> LENGTH: 9
<212> TYPE: PRT
<213> ORGANISM: Artificial
<220> FEATURE:
<223> OTHER INFORMATION: Synthetic FGF-9 analog

<400> SEQUENCE: 30

Arg Thr Gly Phe His Leu Glu Ile Phe
1               5

<210> SEQ ID NO 31
<211> LENGTH: 9
<212> TYPE: PRT
<213> ORGANISM: Artificial
<220> FEATURE:
<223> OTHER INFORMATION: Synthetic FGF-16 analog

<400> SEQUENCE: 31

Arg Thr Gly Phe His Leu Glu Ile Phe
1               5

<210> SEQ ID NO 32
<211> LENGTH: 9
<212> TYPE: PRT
<213> ORGANISM: Artificial
<220> FEATURE:
<223> OTHER INFORMATION: Synthetic FGF-20 analog

<400> SEQUENCE: 32

Arg Thr Gly Phe His Leu Gln Ile Leu
1               5

<210> SEQ ID NO 33
<211> LENGTH: 11
<212> TYPE: PRT
<213> ORGANISM: Artificial
<220> FEATURE:
<223> OTHER INFORMATION: Synthetic FGF-4 analog

<400> SEQUENCE: 33

Asn Val Gly Ile Gly Phe His Leu Gln Ala Leu
1               5                   10

<210> SEQ ID NO 34
<211> LENGTH: 11
<212> TYPE: PRT
<213> ORGANISM: Artificial
<220> FEATURE:
<223> OTHER INFORMATION: Synthetic FGF-6 analog

<400> SEQUENCE: 34

Asn Val Gly Ile Gly Phe His Leu Gln Val Leu
1               5                   10

<210> SEQ ID NO 35
<211> LENGTH: 9
<212> TYPE: PRT
<213> ORGANISM: Artificial
<220> FEATURE:
<223> OTHER INFORMATION: Synthetic FGF-12 analog

<400> SEQUENCE: 35
```

```
Gln Gln Gly Tyr Phe Leu Gln Met His
1               5

<210> SEQ ID NO 36
<211> LENGTH: 9
<212> TYPE: PRT
<213> ORGANISM: Artificial
<220> FEATURE:
<223> OTHER INFORMATION: Synthetic FGF-14 analog

<400> SEQUENCE: 36

Arg Gln Gly Tyr Tyr Leu Gln Met His
1               5

<210> SEQ ID NO 37
<211> LENGTH: 9
<212> TYPE: PRT
<213> ORGANISM: Artificial
<220> FEATURE:
<223> OTHER INFORMATION: Synthetic FGF-13 analog

<400> SEQUENCE: 37

Arg Gln Gly Tyr His Leu Gln Leu Gln
1               5

<210> SEQ ID NO 38
<211> LENGTH: 9
<212> TYPE: PRT
<213> ORGANISM: Artificial
<220> FEATURE:
<223> OTHER INFORMATION: Synthetic FGF-11 analog

<400> SEQUENCE: 38

Arg Gln Gly Phe Tyr Leu Gln Ala Asn
1               5

<210> SEQ ID NO 39
<211> LENGTH: 10
<212> TYPE: PRT
<213> ORGANISM: Artificial
<220> FEATURE:
<223> OTHER INFORMATION: Synthetic FGF-8 analog

<400> SEQUENCE: 39

Arg Thr Ser Gly Lys His Val Gln Val Leu
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic FGF-17 analog

<400> SEQUENCE: 40

Arg Thr Ser Gly Lys His Val Gln Val Thr
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic FGF-18 analog

<400> SEQUENCE: 41
```

Arg Thr Ser Gly Lys His Ile Gln Val Leu
1               5                   10

<210> SEQ ID NO 42
<211> LENGTH: 9
<212> TYPE: PRT
<213> ORGANISM: Artificial
<220> FEATURE:
<223> OTHER INFORMATION: Synthetic FGF-3 analog

<400> SEQUENCE: 42

Ala Thr Lys Tyr His Leu Gln Leu His
1               5

<210> SEQ ID NO 43
<211> LENGTH: 11
<212> TYPE: PRT
<213> ORGANISM: Artificial
<220> FEATURE:
<223> OTHER INFORMATION: Synthetic FGF-5 analog

<400> SEQUENCE: 43

Arg Val Gly Ile Gly Phe His Leu Gln Ile Tyr
1               5                   10

<210> SEQ ID NO 44
<211> LENGTH: 14
<212> TYPE: PRT
<213> ORGANISM: Artificial
<220> FEATURE:
<223> OTHER INFORMATION: Synthetic FGF-19 analog

<400> SEQUENCE: 44

Ser Gly Pro His Gly Leu Ser Ser Cys Phe Leu Arg Ile Arg
1               5                   10

<210> SEQ ID NO 45
<211> LENGTH: 13
<212> TYPE: PRT
<213> ORGANISM: Artificial
<220> FEATURE:
<223> OTHER INFORMATION: Synthetic FGF-21 analog

<400> SEQUENCE: 45

Asp Asp Ala Gln Gln Thr Glu Ala His Leu Glu Ile Arg
1               5                   10

<210> SEQ ID NO 46
<211> LENGTH: 12
<212> TYPE: PRT
<213> ORGANISM: Artificial
<220> FEATURE:
<223> OTHER INFORMATION: Synthetic FGF-23 analog

<400> SEQUENCE: 46

Ala Thr Ala Arg Asn Ser Tyr His Leu Gln Ile His
1               5                   10

<210> SEQ ID NO 47
<211> LENGTH: 13
<212> TYPE: PRT
<213> ORGANISM: Artificial
<220> FEATURE:
<223> OTHER INFORMATION: Synthetic BMP analog

<400> SEQUENCE: 47

Leu Tyr Val Asp Phe Ser Asp Val Gly Trp Asn Asp Trp

<210> SEQ ID NO 48
<211> LENGTH: 15
<212> TYPE: PRT
<213> ORGANISM: Artificial
<220> FEATURE:
<223> OTHER INFORMATION: Synthetic BMP analog

<400> SEQUENCE: 48

Ala Ile Ser Met Leu Tyr Leu Asp Glu Asn Glu Lys Val Val Leu
1               5                   10                  15

<210> SEQ ID NO 49
<211> LENGTH: 17
<212> TYPE: PRT
<213> ORGANISM: Artificial
<220> FEATURE:
<223> OTHER INFORMATION: Synthetic BMP analog

<400> SEQUENCE: 49

Ile Ser Met Leu Tyr Leu Asp Glu Asn Glu Lys Val Val Leu Lys Asn
1               5                   10                  15

Tyr

<210> SEQ ID NO 50
<211> LENGTH: 15
<212> TYPE: PRT
<213> ORGANISM: Artificial
<220> FEATURE:
<223> OTHER INFORMATION: Synthetic BMP analog

<400> SEQUENCE: 50

Glu Lys Val Val Leu Lys Asn Tyr Gln Asp Met Val Val Glu Gly
1               5                   10                  15

<210> SEQ ID NO 51
<211> LENGTH: 16
<212> TYPE: PRT
<213> ORGANISM: Artificial
<220> FEATURE:
<223> OTHER INFORMATION: Synthetic BMP analog

<400> SEQUENCE: 51

Leu Val Val Lys Glu Asn Glu Asp Leu Tyr Leu Met Ser Ile Ala Cys
1               5                   10                  15

<210> SEQ ID NO 52
<211> LENGTH: 16
<212> TYPE: PRT
<213> ORGANISM: Artificial
<220> FEATURE:
<223> OTHER INFORMATION: Synthetic BMP analog

<400> SEQUENCE: 52

Ala Phe Tyr Cys His Gly Glu Cys Pro Phe Pro Leu Ala Asp His Leu
1               5                   10                  15

<210> SEQ ID NO 53
<211> LENGTH: 23
<212> TYPE: PRT
<213> ORGANISM: Artificial
<220> FEATURE:
<223> OTHER INFORMATION: Synthetic BMP analog

<400> SEQUENCE: 53

-continued

```
Pro Phe Pro Leu Ala Asp His Leu Asn Ser Thr Asn His Ala Ile Val
1               5                   10                  15

Gln Thr Leu Val Asn Ser Val
            20
```

<210> SEQ ID NO 54
<211> LENGTH: 27
<212> TYPE: PRT
<213> ORGANISM: Artificial
<220> FEATURE:
<223> OTHER INFORMATION: Synthetic BMP analog

<400> SEQUENCE: 54

```
Thr Gln Leu Asn Ala Ile Ser Val Leu Tyr Phe Asp Asp Ser Ser Asn
1               5                   10                  15

Val Ile Leu Lys Lys Tyr Arg Asn Met Val Val
            20                  25
```

<210> SEQ ID NO 55
<211> LENGTH: 25
<212> TYPE: PRT
<213> ORGANISM: Artificial
<220> FEATURE:
<223> OTHER INFORMATION: Synthetic BMP analog

<400> SEQUENCE: 55

```
His Glu Leu Tyr Val Ser Phe Arg Asp Leu Gly Trp Gln Asp Trp Ile
1               5                   10                  15

Ile Ala Pro Glu Gly Tyr Ala Ala Tyr
            20                  25
```

<210> SEQ ID NO 56
<211> LENGTH: 13
<212> TYPE: PRT
<213> ORGANISM: Artificial
<220> FEATURE:
<223> OTHER INFORMATION: Synthetic Avinin A analog

<400> SEQUENCE: 56

```
Met Leu Tyr Tyr Asp Asp Gly Gln Asn Ile Ile Lys Lys
1               5                   10
```

<210> SEQ ID NO 57
<211> LENGTH: 14
<212> TYPE: PRT
<213> ORGANISM: Artificial
<220> FEATURE:
<223> OTHER INFORMATION: Synthetic Avinin A analog

<400> SEQUENCE: 57

```
Lys Lys Ile Ile Asn Gln Gly Asp Asp Tyr Tyr Leu Met Ser
1               5                   10
```

<210> SEQ ID NO 58
<211> LENGTH: 15
<212> TYPE: PRT
<213> ORGANISM: Artificial
<220> FEATURE:
<223> OTHER INFORMATION: Synthetic Avinin A analog

<400> SEQUENCE: 58

```
Met Leu Tyr Tyr Asp Asp Gly Gln Asn Ile Ile Lys Lys Asp Ile
1               5                   10                  15
```

<210> SEQ ID NO 59

-continued

```
<211> LENGTH: 21
<212> TYPE: PRT
<213> ORGANISM: Artificial
<220> FEATURE:
<223> OTHER INFORMATION: Synthetic TGF-B1 analog

<400> SEQUENCE: 59

Ile Val Tyr Tyr Val Gly Arg Lys Pro Lys Val Glu Gln Leu Ser Asn
1               5                   10                  15

Met Ile Val Arg Ser
            20

<210> SEQ ID NO 60
<211> LENGTH: 22
<212> TYPE: PRT
<213> ORGANISM: Artificial
<220> FEATURE:
<223> OTHER INFORMATION: Synthetic TGF-B2 analog

<400> SEQUENCE: 60

Thr Ile Leu Tyr Tyr Ile Gly Lys Thr Pro Lys Ile Glu Gln Leu Ser
1               5                   10                  15

Asn Met Ile Val Lys Ser
            20

<210> SEQ ID NO 61
<211> LENGTH: 21
<212> TYPE: PRT
<213> ORGANISM: Artificial
<220> FEATURE:
<223> OTHER INFORMATION: Synthetic TGF-B3 analog

<400> SEQUENCE: 61

Leu Thr Ile Leu Tyr Tyr Val Gly Arg Thr Pro Lys Val Glu Gln Leu
1               5                   10                  15

Ser Asn Met Val Val
            20

<210> SEQ ID NO 62
<211> LENGTH: 23
<212> TYPE: PRT
<213> ORGANISM: Artificial
<220> FEATURE:
<223> OTHER INFORMATION: Synthetic BMP-2 analog

<400> SEQUENCE: 62

Ala Ile Ser Met Leu Tyr Leu Asp Glu Asn Glu Lys Val Val Leu Lys
1               5                   10                  15

Asn Tyr Gln Asp Met Val Val
            20

<210> SEQ ID NO 63
<211> LENGTH: 24
<212> TYPE: PRT
<213> ORGANISM: Artificial
<220> FEATURE:
<223> OTHER INFORMATION: Synthetic BMP-3 analog

<400> SEQUENCE: 63

Ser Ser Leu Ser Ile Leu Phe Phe Asp Glu Asn Lys Asn Val Val Leu
1               5                   10                  15

Lys Val Tyr Pro Asn Met Thr Val
            20
```

```
<210> SEQ ID NO 64
<211> LENGTH: 24
<212> TYPE: PRT
<213> ORGANISM: Artificial
<220> FEATURE:
<223> OTHER INFORMATION: Synthetic BMP-3B analog

<400> SEQUENCE: 64

Asn Ser Leu Gly Val Leu Phe Leu Asp Glu Asn Arg Asn Val Val Leu
1               5                   10                  15

Lys Val Tyr Pro Asn Met Ser Val
            20

<210> SEQ ID NO 65
<211> LENGTH: 23
<212> TYPE: PRT
<213> ORGANISM: Artificial
<220> FEATURE:
<223> OTHER INFORMATION: Synthetic BMP-4 analog

<400> SEQUENCE: 65

Ala Ile Ser Met Leu Tyr Leu Asp Glu Tyr Asp Lys Val Val Leu Lys
1               5                   10                  15

Asn Tyr Gln Glu Met Val Val
            20

<210> SEQ ID NO 66
<211> LENGTH: 23
<212> TYPE: PRT
<213> ORGANISM: Artificial
<220> FEATURE:
<223> OTHER INFORMATION: Synthetic BMP-5 analog

<400> SEQUENCE: 66

Ala Ile Ser Val Leu Tyr Phe Asp Asp Ser Ser Asn Val Ile Leu Lys
1               5                   10                  15

Lys Tyr Arg Asn Met Val Val
            20

<210> SEQ ID NO 67
<211> LENGTH: 23
<212> TYPE: PRT
<213> ORGANISM: Artificial
<220> FEATURE:
<223> OTHER INFORMATION: Synthetic BMP-6 analog

<400> SEQUENCE: 67

Ala Ile Ser Val Leu Tyr Phe Asp Asp Asn Ser Asn Val Ile Leu Lys
1               5                   10                  15

Lys Tyr Arg Asn Met Val Val
            20

<210> SEQ ID NO 68
<211> LENGTH: 23
<212> TYPE: PRT
<213> ORGANISM: Artificial
<220> FEATURE:
<223> OTHER INFORMATION: Synthetic BMP-7 analog

<400> SEQUENCE: 68

Ala Ile Ser Val Leu Tyr Phe Asp Asp Ser Ser Asn Val Ile Leu Lys
1               5                   10                  15

Lys Tyr Arg Asn Met Val Val
            20
```

```
<210> SEQ ID NO 69
<211> LENGTH: 23
<212> TYPE: PRT
<213> ORGANISM: Artificial
<220> FEATURE:
<223> OTHER INFORMATION: Synthetic BMP-8 analog

<400> SEQUENCE: 69

Ala Thr Ser Val Leu Tyr Tyr Asp Ser Ser Asn Asn Val Ile Leu Arg
1               5                   10                  15

Lys Ala Arg Asn Met Val Val
            20

<210> SEQ ID NO 70
<211> LENGTH: 23
<212> TYPE: PRT
<213> ORGANISM: Artificial
<220> FEATURE:
<223> OTHER INFORMATION: Synthetic BMP-9 analog

<400> SEQUENCE: 70

Ile Ser Val Leu Tyr Lys Asp Asp Met Gly Val Pro Thr Leu Lys Tyr
1               5                   10                  15

His Tyr Glu Gly Met Ser Val
            20

<210> SEQ ID NO 71
<211> LENGTH: 22
<212> TYPE: PRT
<213> ORGANISM: Artificial
<220> FEATURE:
<223> OTHER INFORMATION: Synthetic BMP-10 analog

<400> SEQUENCE: 71

Ile Ser Ile Leu Tyr Leu Asp Lys Gly Val Val Thr Tyr Lys Phe Lys
1               5                   10                  15

Tyr Glu Gly Met Ala Val
            20

<210> SEQ ID NO 72
<211> LENGTH: 22
<212> TYPE: PRT
<213> ORGANISM: Artificial
<220> FEATURE:
<223> OTHER INFORMATION: Synthetic BMP-11 analog

<400> SEQUENCE: 72

Ile Asn Met Leu Tyr Phe Asn Asp Lys Gln Gln Ile Ile Tyr Gly Lys
1               5                   10                  15

Ile Pro Gly Met Val Val
            20

<210> SEQ ID NO 73
<211> LENGTH: 22
<212> TYPE: PRT
<213> ORGANISM: Artificial
<220> FEATURE:
<223> OTHER INFORMATION: Synthetic BMP-12 analog

<400> SEQUENCE: 73

Ile Ser Ile Leu Tyr Ile Asp Ala Ala Asn Asn Val Val Tyr Lys Gln
1               5                   10                  15

Tyr Glu Asp Met Val Val
            20
```

<210> SEQ ID NO 74
<211> LENGTH: 22
<212> TYPE: PRT
<213> ORGANISM: Artificial
<220> FEATURE:
<223> OTHER INFORMATION: Synthetic BMP-13 analog

<400> SEQUENCE: 74

Ile Ser Ile Leu Tyr Ile Asp Ala Gly Asn Asn Val Val Tyr Lys Gln
1               5                   10                  15

Tyr Glu Asp Met Val Val
            20

<210> SEQ ID NO 75
<211> LENGTH: 22
<212> TYPE: PRT
<213> ORGANISM: Artificial
<220> FEATURE:
<223> OTHER INFORMATION: Synthetic BMP-14 analog

<400> SEQUENCE: 75

Ile Ser Ile Leu Phe Ile Asp Ser Ala Asn Asn Val Val Tyr Lys Gln
1               5                   10                  15

Tyr Glu Asp Met Val Val
            20

<210> SEQ ID NO 76
<211> LENGTH: 22
<212> TYPE: PRT
<213> ORGANISM: Artificial
<220> FEATURE:
<223> OTHER INFORMATION: Synthetic BMP-15 analog

<400> SEQUENCE: 76

Ile Ser Val Leu Met Ile Glu Ala Asn Gly Ser Ile Leu Tyr Lys Glu
1               5                   10                  15

Tyr Glu Gly Met Ile Ala
            20

<210> SEQ ID NO 77
<211> LENGTH: 10
<212> TYPE: PRT
<213> ORGANISM: Artificial
<220> FEATURE:
<223> OTHER INFORMATION: Synthetic PDFG analog

<400> SEQUENCE: 77

Val Arg Lys Ile Glu Ile Val Arg Lys Lys
1               5                   10

<210> SEQ ID NO 78
<211> LENGTH: 24
<212> TYPE: PRT
<213> ORGANISM: Artificial
<220> FEATURE:
<223> OTHER INFORMATION: Synthetic PDFG analog

<400> SEQUENCE: 78

Lys Thr Arg Thr Glu Val Phe Glu Ile Ser Arg Arg Leu Ile Asp Arg
1               5                   10                  15

Thr Asn Ala Asn Phe Leu Val Trp
            20

<210> SEQ ID NO 79
<211> LENGTH: 16
<212> TYPE: PRT
<213> ORGANISM: Artificial
<220> FEATURE:
<223> OTHER INFORMATION: Synthetic PDFG analog

<400> SEQUENCE: 79

Gln Val Arg Lys Ile Glu Ile Val Arg Lys Lys Pro Ile Phe Lys Lys
1               5                   10                  15

<210> SEQ ID NO 80
<211> LENGTH: 15
<212> TYPE: PRT
<213> ORGANISM: Artificial
<220> FEATURE:
<223> OTHER INFORMATION: Synthetic BMP analog

<400> SEQUENCE: 80

Leu Val Val Lys Glu Asn Glu Asp Leu Tyr Leu Met Ser Ile Ala
1               5                   10                  15

<210> SEQ ID NO 81
<211> LENGTH: 17
<212> TYPE: PRT
<213> ORGANISM: Artificial
<220> FEATURE:
<223> OTHER INFORMATION: Synthetic BMP analog

<400> SEQUENCE: 81

Tyr Asn Lys Leu Val Val Lys Glu Asn Glu Asp Leu Tyr Leu Met Ser
1               5                   10                  15

Ile

<210> SEQ ID NO 82
<211> LENGTH: 13
<212> TYPE: PRT
<213> ORGANISM: Artificial
<220> FEATURE:
<223> OTHER INFORMATION: Synthetic BMP analog

<400> SEQUENCE: 82

Lys Lys Leu Ile Val Asn Ser Ser Glu Asp Phe Tyr Leu
1               5                   10

<210> SEQ ID NO 83
<211> LENGTH: 13
<212> TYPE: PRT
<213> ORGANISM: Artificial
<220> FEATURE:
<223> OTHER INFORMATION: Synthetic BMP analog

<400> SEQUENCE: 83

Trp Asp Asn Trp Gly Val Asp Ser Phe Asp Val Tyr Leu
1               5                   10

<210> SEQ ID NO 84
<211> LENGTH: 15
<212> TYPE: PRT
<213> ORGANISM: Artificial
<220> FEATURE:
<223> OTHER INFORMATION: Synthetic BMP analog

<400> SEQUENCE: 84

Gly Glu Val Val Met Asp Gln Tyr Asn Lys Leu Val Val Lys Glu
1               5                   10                  15

```
<210> SEQ ID NO 85
<211> LENGTH: 16
<212> TYPE: PRT
<213> ORGANISM: Artificial
<220> FEATURE:
<223> OTHER INFORMATION: Synthetic BMP analog

<400> SEQUENCE: 85

Leu His Asp Ala Leu Pro Phe Pro Cys Glu Gly His Cys Tyr Phe Ala
1               5                   10                  15

<210> SEQ ID NO 86
<211> LENGTH: 23
<212> TYPE: PRT
<213> ORGANISM: Artificial
<220> FEATURE:
<223> OTHER INFORMATION: Synthetic BMP analog

<400> SEQUENCE: 86

Val Ser Asn Val Leu Thr Gln Val Ile Ala His Asn Thr Ser Asn Leu
1               5                   10                  15

His Asp Ala Leu Pro Phe Pro
            20

<210> SEQ ID NO 87
<211> LENGTH: 16
<212> TYPE: PRT
<213> ORGANISM: Artificial
<220> FEATURE:
<223> OTHER INFORMATION: Synthetic BMP analog

<400> SEQUENCE: 87

Leu Val Val Lys Glu Asn Glu Asp Leu Tyr Leu Met Ser Ile Ala Cys
1               5                   10                  15

<210> SEQ ID NO 88
<211> LENGTH: 28
<212> TYPE: PRT
<213> ORGANISM: Artificial
<220> FEATURE:
<223> OTHER INFORMATION: Synthetic FGF analog

<400> SEQUENCE: 88

Ala Glu Ser Gly Asp Asp Tyr Cys Val Leu Val Phe Thr Asp Ser Ala
1               5                   10                  15

Trp Thr Lys Ile Cys Asp Trp Ser His Phe Arg Asn
            20                  25

<210> SEQ ID NO 89
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 89

Arg Lys Leu Ala Val Tyr Trp Ser Ser Tyr Lys Arg Ser Arg Tyr
1               5                   10                  15

<210> SEQ ID NO 90
<211> LENGTH: 17
<212> TYPE: PRT
<213> ORGANISM: Artificial
<220> FEATURE:
<223> OTHER INFORMATION: Synthetic FGF-1 analog
```

```
-continued

<400> SEQUENCE: 90

Lys Lys Leu Gly Val Phe Trp Asn Lys Glu Ala His Lys Lys Ser Ile
1               5                   10                  15

Tyr

<210> SEQ ID NO 91
<211> LENGTH: 15
<212> TYPE: PRT
<213> ORGANISM: Artificial
<220> FEATURE:
<223> OTHER INFORMATION: Synthetic FGF-1 analog

<400> SEQUENCE: 91

Tyr Val Glu Gly Val Glu Ser Ala Ser Leu Gln Leu Gln Ile His
1               5                   10                  15

<210> SEQ ID NO 92
<211> LENGTH: 20
<212> TYPE: PRT
<213> ORGANISM: Artificial
<220> FEATURE:
<223> OTHER INFORMATION: Synthetic FGF-7 analog

<400> SEQUENCE: 92

Lys Gln Asn Leu Ala Val Phe Met Glu Gly Gly Asn His Thr Trp Lys
1               5                   10                  15

Ala Ser Ala Tyr
            20

<210> SEQ ID NO 93
<211> LENGTH: 15
<212> TYPE: PRT
<213> ORGANISM: Artificial
<220> FEATURE:
<223> OTHER INFORMATION: Synthetic FGF-7 analog

<400> SEQUENCE: 93

Ala Val Ile Gly Val Ala Val Thr Arg Ile Glu Met Ile Asn Tyr
1               5                   10                  15
```

FORMULATIONS AND METHODS FOR DELIVERY OF GROWTH FACTOR ANALOGS

CROSS-REFERENCE TO RELATED APPLICATIONS

This application claims priority to and the benefit of the filing of U.S. Provisional Patent Application Ser. No. 60/656,714, entitled "Formulations and Methods for Delivery of Growth Factor Analogs", filed on Feb. 25, 2005; U.S. Provisional Patent Application Ser. No. 60/656,713, entitled "Cysteine-Branched Heparin-Binding Growth Factor Analogs", filed on Feb. 25, 2005; and U.S. Provisional Patent Application Ser. No. 60/656,174, entitled "TGF Growth Factor Analogs", filed on Feb. 25, 2005; and the specification and claims thereof of each are incorporated herein by reference.

REFERENCE TO A SEQUENCE LISTING, A TABLE, OR COMPUTER PROGRAM

This application includes a "Sequence Listing" filed herewith under 37 C.F.R. § 1.821(c) on disc in accordance with 37 C.F.R. § 1.821(d). Two identical copies (marked "Copy 1" and "Copy 2") of said disc, both of which contain said "Sequence Listing," are submitted herewith, for a total of two discs submitted. Said "Sequence Listing" is recorded on said discs as "30817formulations.ST25.txt" created Feb. 23, 2006, size 23.5 KB, 24,064 bytes, which is hereby incorporated by reference in this application in its entirety.

This application is a continuation-in-part of U.S. patent application Ser. No. 11/167,636, entitled "Bioactive Peptide Coatings", filed on Jun. 27, 2005, which in turn was a continuation-in-part application of U.S. patent application Ser. No. 11/055,428, entitled "Heterodimeric Chain Synthetic Heparin-Binding Growth Factor Analogs", filed on Feb. 10, 2005 now U.S. Pat. No. 7,528,105, which in turn claimed priority to and the benefit of the filing of U.S. Provisional Patent Application Ser. No. 60/543,616, entitled "Heterodimeric Chain Synthetic Heparin-Binding Growth Factor Analogs", filed on Feb. 10, 2004, and the specification and claims thereof of each are incorporated herein by reference.

This application is also a continuation-in-part of U.S. patent application Ser. No. 11/359,173, which is "Single Branch Heparin-Binding Growth Factor," filed on Feb. 21, 2006, which in turn claimed priority to and the benefit of the filing of U.S. Provisional Patent Application Ser. No. 60/655,570, entitled "Single Branch Heparin-Binding Growth Factor," filed on Feb. 22, 2005, and the specification and claims thereof of each are incorporated herein by reference.

BACKGROUND OF THE INVENTION

1. Field of the Invention (Technical Field)

The present invention relates to formulations, methods and kits for the delivery and administration of synthetic heparin-binding growth factor analogs, particularly for use in tissue repair, including bone and cartilage repair.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

The use of various bone filler agents and compositions is well known. Among materials used are various calcium-containing compounds and compositions including demineralized bone matrix (DBM). Limited research has been conducted using compositions which include growth factors, including recombinantly-produced growth factors, such as recombinantly produced bone morphogenic protein-2 (BMP-2).

The role of other growth factors in tissue repair, such as transforming growth factor-alpha (TGF-α) or transforming growth factor-beta (TGF-β), has been studied. In particular, TGF-β is known to accelerate the wound repair process. TGF-β1 has been proposed as a likely candidate for stimulating cartilage repair as it affects chondrocytes by enhancing matrix production, cell proliferation, and osteochondrogenic differentiation. There are at least three isoforms of TGF-β in man, TGF-β1, TGF-β2, TGF-β3. TGF-β exists in at least five isoforms, known TGF-β1, TGF-β2, TGF-β3, TGF-β4 and TGF-β5, that are not related to TGF-α. Their amino acid sequences display homologies on the order of 70-80 percent. TGF-β1 is the prevalent form and is found almost ubiquitously while the other isoforms are expressed in a more limited spectrum of cells and tissues.

TGF-beta is the prototype of a family of proteins known as the TGF-beta superfamily. This family includes inhibins, Activin A, MIS (Mullerian activating substance) and BMPs (Bone morphogenic proteins). Burt, Evolutionary grouping of the transforming growth factor-beta superfamily. *Biochem. Biophys. Res. Commun.* 184:590-5 (1992).

Some 23 fibroblast growth factors identified to date (FGFs 1-23). Peptides from natural HBGFs that bind heparin-binding growth factor receptors have been identified. See for example Ray et al., *Proc. Natl. Acad. Sci. USA* 94:7047-7052 (1997). FGFs useful in prevention or therapy of a wide range of diseases and disorders may be purified from natural sources or produced by recombinant DNA methods; however, such preparations are expensive and generally difficult to prepare.

However, there are no known formulations, methods or kits designed to provide components that augment or activate growth factors, such as FGF-2, BMP-2 or TGF-β, which may be present endogenously, such as produced by the individual being treatment, or which may be exogenous, such as derived from natural material or produced by recombinant means. There are further no known formulations, methods or kits that employ the synthetic heparin-binding growth factor analogs disclosed herein. It is against this background that the invention is made.

BRIEF SUMMARY OF THE INVENTION

In one aspect the invention provides a formulation for bone or cartilage repair, which formulation includes a synthetic heparin-binding growth factor analog comprising at least one sequence of amino acid residues binding a heparin-binding growth factor receptor (HBGFR), a hydrophobic linker region and a heparin-binding region, wherein the HBGFR is a member of the TGF-beta superfamily, the FGF family or the PDGF family and a calcium-containing agent, and optionally further includes a non-ionic polymer and a gelling agent. The formulation may include a synthetic heparin-binding growth factor analog such as B2A2-K-NS or F2A4-K-NS. The synthetic heparin-binding growth factor analog may be of any of formulas I to XIV hereafter set forth, and include, in whole or part, any one or more of SEQ ID NO:1 through SEQ ID NO:93.

Where provided, the non-ionic polymers may include ethylenoxide and propylenoxide block-copolymers. The gelling agent may include sodium carboxymethylcellulose, hydroxypropyl cellulose, carboxymethylcellulose, hydroxypropyl(methyl) cellulose, agar, alginates, hyaluronic acid, heparin, dextran sulfate, gelatin, collagen or a mixture of any of the foregoing. The calcium-containing agent may include calcium sulfate dihydrate, anhydrous calcium sulfate, dicalcium phosphate, tricalcium phosphate, calcium sulfate hemihydrate, calcium sulfate dihydrate, pentacalcium hydroxyl apatite (hydroxyapatite), tetracalcium phosphate monoxide or a mixture of any of the foregoing.

In another aspect, the formulation may further include demineralized bone matrix. In yet another aspect, the formulation may further include bone marrow, bone marrow cells, bone chips or morselized bone.

The invention further provides a kit for making an injectable formulation for bone or cartilage repair, the kit including a first syringe containing an aqueous solution including a non-ionic polymer, a gelling agent and a calcium-containing agent; and a vial containing a preparation including a synthetic heparin-binding growth factor analog comprising at least one sequence of amino acid residues binding a heparin-binding growth factor receptor (HBGFR), a hydrophobic linker region and a heparin-binding region, wherein the HBGFR is a member of the TGF-beta superfamily, the FGF family or the PDGF family. In the kit, the synthetic heparin-binding growth factor analog may further be characterized in that it augments cell growth or differentiation. The kit may further include a second syringe and a mixing hub for interconnecting the first syringe and second syringe.

The invention further provides a method of treating an osteogenic defect in a patient, the method including providing a preparation in the form of a solution, gel or putty and including a synthetic heparin-binding growth factor analog comprising at least one sequence of amino acid residues binding a heparin-binding growth factor receptor (HBGFR), a hydrophobic linker region and a heparin-binding region, wherein the HBGFR is a member of the TGF-beta superfamily, the FGF family or the PDGF family and a calcium-containing agent; and delivering the preparation to a site comprising the osteogenic defect. The osteogenic defect may include a bone fracture, a boney void or two or more vertebrae to be fused.

A primary object of the present invention is to provide novel compositions and methods for use in tissue repair, including bone and cartilage repair.

Another object of the present invention is to provide compositions which include a calcium-containing agent and a synthetic heparin-binding growth factor analog comprising at least one sequence of amino acid residues binding a heparin-binding growth factor receptor.

Another object of the present invention is to provide compositions which include a calcium-containing agent and a synthetic heparin-binding growth factor analog of any of formulas I to XIV.

Another object of the present invention is to provide compositions which include a synthetic heparin-binding growth factor analog of any of formulas I to XIV formulated as a gel, paste or sol.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
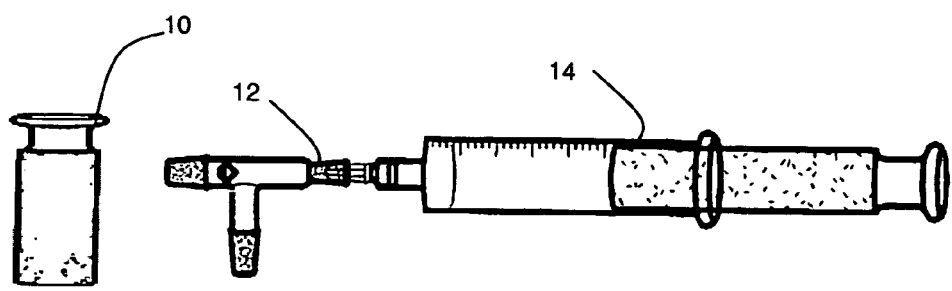
FIGS. 1, 2 and 3 are views of aspects of a kit of the present invention, including a vial containing synthetic heparin-binding growth factor analog, syringes, including one preloaded with a calcium-containing gel, and a three-way value.

Each synthetic HBGF analog utilized in the invention is an analog of a particular HBGF that binds to one or more of the receptors bound by the particular HBGF. The synthetic HBGF analog may be an analog of a hormone, a cytokine, a lymphokine, a chemokine or an interleukin.

In one aspect the synthetic HBGF analog of the present invention is a molecule comprising amino acid residues binding a heparin-binding growth factor receptor (HBGFR), a hydrophobic linker region and a heparin-binding region. HBGFs include any growth factor that binds selectively to heparin. Of particular utility herein are HBGFs which are useful or may be employed in bone or cartilage repair or remodeling, which include specifically the FGF (fibroblast growth factors) family, such as the known FGF subtypes (FGF-1 to FGF-23), the TGF-β (transforming growth factor-β) family, sometimes called the TGF-β superfamily, which includes therein the TGF-β isoforms and distinct sub-families, including the BMP (bone morphogenic protein) family, and the PDGF (platelet derived growth factor) family.

In particular embodiments of the present invention, the HBGF analog is a synthetic analog comprising amino acid residues binding a HBGFR, a hydrophobic linker region and a heparin-binding region. Thus, in particular embodiments the synthetic HBGF analog of the present invention may consist of constructs of any of the following formulas.

In one embodiment, the coating and methods utilize a HBGF analog of formula I:

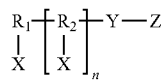

I wherein each X is a peptide chain that (i) has a minimum of three amino acid residues, (ii) has a maximum of about fifty amino acid residues, and (iii) binds a heparin-binding growth factor receptor (HBGFR); $R_1$ is an amino acid residue, wherein X is covalently bonded through the N-terminus of $R_1$ or through a side chain of $R_1$; $R_2$ is a trifunctional alpha amino acid residue, wherein X is covalently bonded through a side chain of $R_2$; Y is a linker comprising a chain from 0 to about 50 atoms covalently bonded to $R_1$ and Z when n=0, or to $R_2$ and Z when n=1; Z is a non-signaling peptide chain that comprises a heparin binding domain, comprising an amino acid sequence that comprises (i) a minimum of one heparin binding motif, (ii) a maximum of about ten heparin binding motifs, and (iii) a maximum of about thirty amino acids; and, n is 0 or 1, wherein when n=1 the peptide chains X are identical.

In the HBGF analog of formula I, Y is a linker that (i) is hydrophobic, (ii) comprises a chain of a minimum of about 9 and a maximum of about 50 atoms, and (iii) is preferably not found in the natural ligand of the HBGFR which X binds. In one embodiment of formula I, $R_1$ is a trifunctional amino acid residue, wherein X is covalently bonded through a side chain of $R_1$.

In one embodiment of formula I, the HBGF analog of formula I is characterized in that it has an avidity for heparin such that the it binds heparin in 0.15 M NaCl, but is eluted by 1 M NaCl.

In another embodiment, the coating and methods utilize a HBGF analog of formula II:

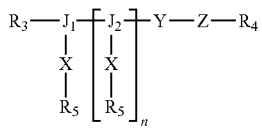

II wherein $R_3$ and $R_5$ are each independently $NH_2$, an acyl group with a linear or branched $C_1$ to $C_{17}$ alkyl, aryl, heteroaryl, alkene, alkenyl or aralkyl chain including a N-terminus $NH_2$, $NH_3^+$, or NH group or a corresponding acylated derivative, or is an amino acid, a dipeptide or a tripeptide, with an N-terminus $NH_2$, $NH_3^+$, NH group or a corresponding acylated derivative; $R_4$ is —OH, $NH_2$, NH—$R_6$, or is an amino acid, a dipeptide or a tripeptide with a C-terminus —OH, $NH_2$, or NH—$R_6$; $R_6$ is an aliphatic $C_1$ to $C_{17}$ chain; each X is a peptide chain defined as above; $J_1$ and $J_2$ are each independently a trifunctional alpha amino acid residue, wherein each X is covalently bonded through a side chain of $J_1$ or $J_2$; Y is a linker defined as above covalently bonded to $J_1$ and Z when n=0, or to $J_2$ and Z when n=1; Z is a non-signaling peptide defined as above; and, n is 0 or 1, wherein when n=1 the synthetic peptide chains X are identical.

In the HGBF analog of formula II, Y is a linker that (i) hydrophobic, (ii) comprises a chain of a minimum of about 9 and a maximum of about 50 atoms, and (iii) is not preferably found in the natural ligand of the HBGFR which X binds.

In one embodiment, the HBGF analog of formula II is characterized in that it has an avidity for heparin such that it binds heparin in 0.15 M NaCl, but is eluted by 1 M NaCl.

The HBGF analog of formula II can further be characterized in that binding of it to the HBGFR initiates a signal by the HBGFR, or alternatively in that it blocks signaling by the HBGFR.

In one embodiment of the HBGF analog of formula II, $J_1$ and, if n=1, $J_2$, is a diamine amino acid residue. Such diamine amino acid residue may be a 2,3 diamino propionyl amino acid residue, a lysyl residue or an ornithinyl residue. In an alternative embodiment of the HBGF analog of formula II, the side chain of $J_1$ and, if n=1, $J_2$, includes a reactive carboxyl group.

In one embodiment of the HBGF analog of formula II, the covalent bond between X and $J_1$ or, if n=1, $J_2$, comprises an amide, disulfide, thioether, Schiff base, reduced Schiff base, imide, secondary amine, carbonyl, urea, hydrazone or oxime bond. In a preferred embodiment, the bond is an amide bond.

The HBGF analog of formula II thus includes a HBGF analog of formula III:

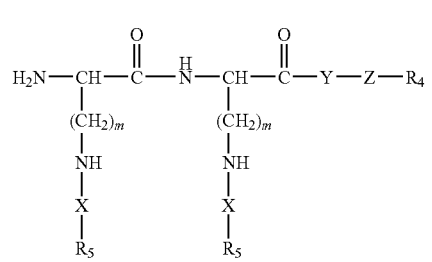

III wherein m is from 1 to about 10.

The HBGF analog of formula III thus further includes a HBGF analog of formula IV:

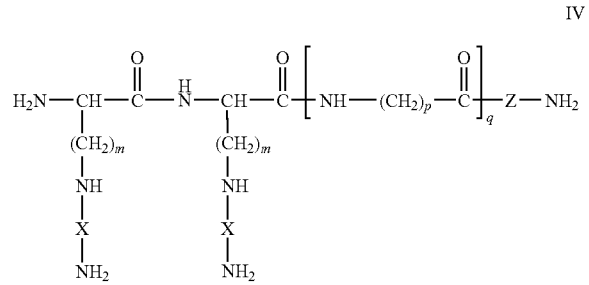

IV wherein p is from 1 to about 10 and q is from 1 to about 20. In one particularly preferred embodiment, p is 5 and q is three.

In one embodiment, in the HBGF analog of any of formula I or II where n=1, or of formula III or IV, the peptide chains X are cross-linked or cyclized. Such cross-linking or cyclization may be through a covalent bond, including at least one disulfide, peptide, amide or thioether bond.

In another embodiment, in the HBGF analog of any of formula I, II or III, Y includes between one and about thirty-three ethylene glycol (oxyethylene) units. Alternatively, Y may include a hydrophobic branched or unbranched, saturated or unsaturated alkyl chain of between one and about twenty carbon atoms. In a particularly preferred embodiment, Y is $[NH_2\text{—}(CH_2)_p(C\text{=}O)]_q$ wherein p is from 1 to about 10 and q is from 1 to about 20. In another embodiment, Y includes a peptide sequence, and in a preferred embodiment, with from one to about 16 Gly residues.

In another embodiment of the HBGF analog of any of formula I, II, III or IV, each heparin binding motif of Z is BxBB, or BBBxxB, wherein each B independently represents lysine, arginine, ornithine, or histidine, and x represents a naturally occurring amino acid. In a preferred embodiment, Z includes at least two heparin-binding motifs, more preferably at least five heparin-binding motifs.

In another embodiment, the HBGF analog may be a molecule comprising two different amino acid residues each binding a different HBGFR, a hydrophobic linker region and a heparin-binding region. Thus the HBGF analog employed in this invention may one of formula V:

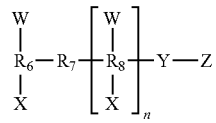

wherein each X and each W is a peptide chain differing by at least one amino acid residue that (i) has a minimum of three amino acid residues, (ii) has a maximum of about fifty amino acid residues, and (iii) binds a heparin-binding growth factor receptor (HBGFR); $R_6$ is a trifunctional amino acid residue covalently bonded to W and X or a dipeptide of the formula $AA_1\text{-}AA_2$; $R_7$ is a linker comprising a chain from 3 to about 20 atoms covalently bonded to $R_6$ and Y when n=0, or to $R_6$ and $R_8$ when n=1; $R_8$ is a dipeptide of the formula $AA_2\text{-}AA_2$; Y is a linker as defined above; Z is a non-signaling peptide chain that includes a heparin binding domain as defined above. Where provided, $AA_1$ is an amino acid residue, wherein one of X or W is covalently bonded through the N-terminus of $AA_1$ or through a side chain of $AA_1$; $AA_2$ is in each instance independently a trifunctional amino acid residue, wherein one of X or W is covalently bonded through a side chain of $AA_2$; and, n is 0 or 1.

In a preferred embodiment of the heparin-binding growth factor analog of formula V, X, W and Z are synthetic peptide chains. In the HBGF analog of formula V, Y can further consist of a linker that (i) is hydrophobic, (ii) comprises a chain of a minimum of about 9 and a maximum of about 50 atoms, and (iii) is not found in the natural ligand of the heparin-binding growth factor receptor (HBGFR) which X or W binds. In one embodiment of the HBGF analog of formula I, $R_6$ is a trifunctional amino acid residue, wherein X is covalently bonded through a side chain of $R_6$. The HBGF analog of formula V may be characterized, in certain embodiments, as having an avidity for heparin such that the HBGF analog binds heparin in 0.15 M NaCl, but is eluted by 1 M NaCl.

In another embodiment, the invention provides a HBGF of formula VI:

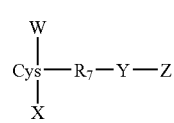

wherein Cys is cysteine; $R_7$ is a linker consisting of a sulfhydryl reactive homo-bifunctional cross-linker and a second Cys or comprising a hetero-bifunctional cross-linker; and W, X, Y and Z are as defined for formula V.

In yet another embodiment, the HBGF analog may be a construct of formula VII:

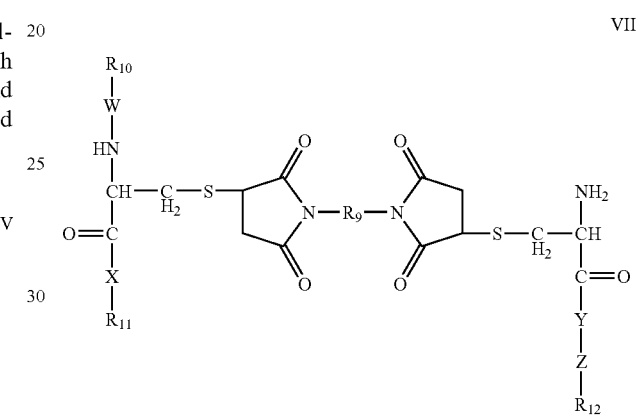

wherein $R_9$ is a linker comprising a chain of between 1 and about 10 backbone atoms selected from carbon, oxygen, sulfur and nitrogen or mixtures thereof; $R_{10}$ is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative; $R_{11}$ is OH, $NH_2$, or NH—$R_{10}$; $R_{12}$ is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative; and W, X, Y and Z are as defined for formula V.

In yet another embodiment, the HBGF may be a construct of formula VIII:

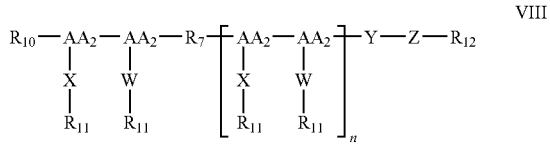

wherein $R_7$, $R_{10}$, $R_{11}$, and $R_{12}$ are as defined above; $AA_2$ is in each instance independently a trifunctional amino acid residue, wherein each X or W is covalently bonded through a side chain of $AA_2$; and X, W, Y and Z are as defined in formula V.

In the constructs of formulas V, VI or VIII, $AA_2$ may be in each instance a diamine amino acid residue, including a 2,3 diamino propionyl amino acid residue, a 2,4 diamino butylic amino acid residue, lysine or ornithine.

In the HBGF analogs of formula V, covalent bonds between $R_6$ and $R_7$ and between $R_7$ and Z when n=0, or between $R_8$ and Z when n=1, can be an amide, disulfide, thioether, Schiff base, reduced Schiff base, imide, secondary amine, carbonyl, urea, hydrazone or oxime bond.

In one embodiment of the HBGF of formulas V, VI or VIII, the side chains of $AA_1$ and $AA_2$ can include reactive carboxyl groups.

In another embodiment, the HBGF analog may be a molecule comprising two identical amino acid residues binding a HBGFR, but separated by a spacer sequence, and further with a hydrophobic linker region and a heparin-binding region. Thus the HBGF analog employed in this invention may one of formula IX:

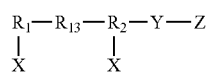

wherein each X is a peptide chain that (i) has a minimum of three amino acid residues, (ii) has a maximum of about fifty amino acid residues, and (iii) binds a heparin-binding growth factor receptor (HBGFR); $R_1$ is an amino acid residue, wherein X is covalently bonded through the N-terminus of $R_1$ or through a side chain of $R_1$; $R_{13}$ is a linker comprising a chain from 3 to about 20 backbone atoms covalently bonded to $R_1$ and $R_2$; $R_2$ is a trifunctional alpha amino acid residue, wherein X is covalently bonded through a side chain of $R_2$; Y is a linker comprising a chain from 0 to about 50 backbone atoms covalently bonded to $R_2$ and Z; and Z is a non-signaling peptide chain that comprises a heparin binding domain, comprising an amino acid sequence that comprises (i) a minimum of one heparin binding motif, (ii) a maximum of about ten heparin binding motifs.

In the HBGF analog of formula IX, $R_{13}$ can further include a linker that (i) comprises a chain of a minimum of about 3 and a maximum of about 20 atoms, and (ii) is not found in the natural ligand of the HBGFR which X binds. $R_{13}$ can further include a linker comprising a repeat unit, such as for example amino hexanoic acid (Hex) repeat units or amino acid repeat units, such as Gly repeats.

In the HBGF analog of formula IX, Y can further include a linker that (i) is hydrophobic, (ii) comprises a chain of a minimum of about 9 and a maximum of about 50 atoms, and (iii) is not found in the natural ligand of the HBGFR which X binds. In one embodiment of formula IX, $R_1$ is a trifunctional amino acid residue, wherein X is covalently bonded through a side chain of $R_1$.

In one embodiment of formula IX, the HBGF analog of formula IX is characterized in that it has an avidity for heparin such that the it binds heparin in 0.15 M NaCl, but is eluted by 1 M NaCl.

In another embodiment, the invention provides an HBGF analog of formula X:

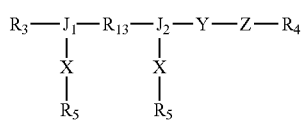

wherein $R_3$ and $R_5$ are each independently $NH_2$, an acyl group with a linear or branched $C_1$ to $C_{17}$ alkyl, aryl, heteroaryl, alkene, alkenyl or aralkyl chain including a N-terminus $NH_2$, $NH_3^+$, or NH group or a corresponding acylated derivative, or is an amino acid, a dipeptide or a tripeptide, with an N-terminus $NH_2$, $NH_3^+$, NH group or a corresponding acylated derivative; $R_4$ is —OH, $NH_2$, NH—$R_{14}$, or is an amino acid, a dipeptide or a tripeptide with a C-terminus —OH, $NH_2$, or NH—$R_{14}$; $R_{14}$ is an aliphatic $C_1$ to $C_{17}$ chain; each X is a peptide chain that (i) has a minimum of three amino acid residues, (ii) has a maximum of about fifty amino acid residues, and (iii) binds a HBGFR; $J_1$ and $J_2$ are each independently a trifunctional alpha amino acid residue, wherein each X is covalently bonded through a side chain of $J_1$ or $J_2$; $R_{13}$ is a linker comprising a chain from 3 to about 20 backbone atoms covalently bonded to $J_1$ and $J_2$; Y is a linker comprising a chain from 0 to about 50 backbone atoms covalently bonded to $J_2$ and Z; and Z is a non-signaling peptide that comprises a heparin binding domain, comprising an amino acid sequence that comprises (i) a minimum of one heparin binding motif, (ii) a maximum of about ten heparin binding motifs, and (iii) a maximum of about thirty amino acids.

In the HBGF analog of formula X, $R_{13}$ can further include a linker that (i) comprises a chain of a minimum of about 1 and a maximum of about 20 atoms, and (ii) is not found in the natural ligand of the HBGFR which X binds. $R_{13}$ can further include a linker comprising a repeat unit, such as for example Hex repeat units or amino acid repeat units, such as Gly repeats.

In the HGBF analog of formula X, Y further preferably includes a linker that (i) hydrophobic, (ii) comprises a chain of a minimum of about 9 and a maximum of about 50 atoms, and (iii) is not found in the natural ligand of the HBGFR which X binds.

In one embodiment, the HBGF analog of formula X is characterized in that it has an avidity for heparin such that it binds heparin in 0.15 M NaCl, but is eluted by 1 M NaCl.

The HBGF analog of formula X can further be characterized in that binding of it to the HBGFR initiates a signal by the HBGFR, or alternatively in that it blocks signaling by the HBGFR.

In one embodiment of the HBGF analog of formula X, $J_1$ and, if n=1, $J_2$, is a diamine amino acid residue. Such diamine amino acid residue may be a 2,3 diamino propionyl amino acid residue, a 2,4 diamino butylic amino acid residue, a lysyl residue or an ornithinyl residue. In an alternative embodiment of the HBGF analog of formula II, the side chain of $J_1$ and, if n=1, $J_2$, includes a reactive carboxyl group.

In one embodiment of the HBGF analog of formula X, the covalent bond between X and $J_1$ or, if n=1, $J_2$, comprises an amide, disulfide, thioether, Schiff base, reduced Schiff base, imide, secondary amine, carbonyl, urea, hydrazone or oxime bond. In a preferred embodiment, the bond is an amide bond. The HBGF analog of formula X thus further includes a HBGF analog of formula XI:

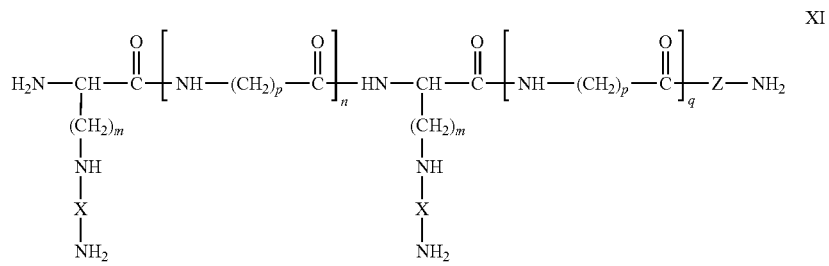

XI wherein each m is independently from 1 to about 10, each p is independently from 1 to about 10, q is from 1 to about 20, and n is from 1 to about 6. In one particularly preferred embodiment, p is 5, q is 3, m is 4, and n is 3.

In another embodiment, there is provided a HBGF analog of formula XII:

$$R_3-X-R_2-R_1-Y-Z-R_4$$
$$|$$
$$R_2$$
$$|$$
$$X$$
$$|$$
$$R_3$$

XII wherein each X is a peptide chain that (i) has a minimum of three amino acid residues, (ii) has a maximum of about fifty amino acid residues, and (iii) binds a heparin-binding growth factor receptor (HBGFR); $R_1$ is a single trifunctional amino acid residue covalently bonded to each X; each $R_2$ is independently a linker comprising a chain from 0 to about 20 backbone atoms including carbon, oxygen, sulfur, nitrogen and mixtures thereof covalently bonded to $R_1$ and X; each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative; $R_4$ is OH such that the terminal group is carboxyl, or is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or $NH-R_3$; Y is a linker comprising a chain from 0 to about 50 backbone atoms covalently bonded to $R_1$ and Z; and Z is a non-signaling peptide chain that includes a heparin binding domain, comprising an amino acid sequence that comprises (i) a minimum of one heparin binding motif, (ii) a maximum of about ten heparin binding motifs, and (iii) a maximum of about thirty amino acids.

The HPBG analog of formula XII thus further includes a HBGF analog of formula XIII:

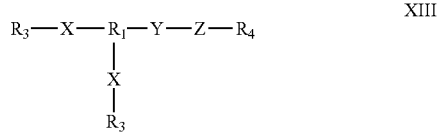

XIII wherein $R_1$ is a diamine amino acid. The diamine amino acid may be an L- or D-diamine amino acid, including L- or D-isomers of 2,3 diamino propionyl amino acid, 2,4 diamino butylic amino acid, lysine or ornithine.

In one particularly preferred embodiment, HBGF analog of either formula XII or XIII further is a HBGF analog of formula XIV:

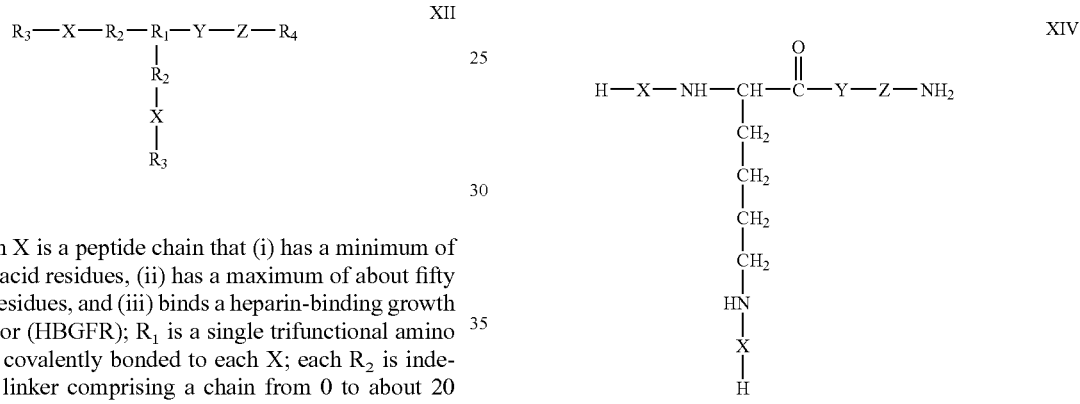

XIV wherein C is carbon, H is hydrogen, N is nitrogen and O is oxygen, and X, Y and Z are as defined for formula XII.

In one embodiment, in the HBGF analog of the foregoing formulas, the peptide chains X are cross-linked or cyclized. Such cross-linking or cyclization may be through a covalent bond, including at least one disulfide, peptide, amide or thioether bond. In another embodiment, the terminal amines of each X, if provided, are crosslinked by means of a dialdehyde or by conjugation with a bifunctional crosslinking agent containing maleimides, aldehydes, succinymidal esters, benzotriazole carbonate, para-nitrophenol, or the like.

In another embodiment, the HBGF analog of any of the foregoing formulas includes between one and about thirty-three ethylene glycol (oxyethylene) units. Alternatively, Y may include a branched or unbranched, saturated or unsaturated alkyl chain of between one and about twenty carbon atoms. In a particularly preferred embodiment, Y is $[NH_2-(CH_2)_p(C=O)]_q$ wherein p is from 1 to about 10 and q is from 1 to about 20. In another embodiment, Y includes a peptide sequence, and in a preferred embodiment, with from one to about 16 Gly residues.

The Heparin-Binding Growth Factors of the Foregoing Formulas

The regions X and Z of the synthetic HBGF analogs of the foregoing formulas include amino acid residues, and optionally the region Y includes amino acid residues. An amino acid residue is defined as $-NHRCO-$, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, Y and Z component regions of the synthetic HBGF analogs of the invention can include any of the twenty amino acids found naturally in proteins, i.e. alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y and Z component regions of the synthetic HBGF analogs of the invention can include any of the naturally occurring amino acids not found naturally in proteins, e.g. β-alanine, betaine (N,N,N-trimethylglycine), homoserine, homocysteine, γ-amino butyric acid, ornithine, and citrulline.

Additionally, the amino acids of the X, Y and Z component regions of the synthetic HBGF analogs of the invention can include any of the non-biological amino acids, i.e. those not normally found in living systems, such as for instance, a straight chain amino-carboxylic acid not found in nature. Examples of straight chain amino-carboxylic acids not found in nature include 6-aminohexanoic acid, and 7-aminoheptanoic acid, 9-aminononanoic acid and the like.

The amino acid $R_1$ of formula I or any of the foregoing formulas can be any of the amino acids described above. $R_2$ of formula I or any of the foregoing formulas, and $J_1$ and $J_2$ of formula II or any of the foregoing formulas, can be any trifunctional amino acid residue, preferably a trifunctional alpha amino acid residue. In a preferred embodiment, the trifunctional amino acid residue is a diamine amino acid, such as for instance lysine or ornithine, or any other amino acid having two amino groups.

The region X and, if provided, the region W of the foregoing formulas of synthetic HBGF analogs is a synthetic peptide chain that binds an HBGFR. Region X or W can, for example, have any amino acid sequence that binds an HBGFR, and can include amino acid sequences that are identical to a portion of the amino acid sequence of a HBGF. Alternatively, X or W can have an amino acid sequence homologous rather than identical to the amino acid sequence of an HBGF. The particular HBGFR bound by the synthetic HBGF analog of the invention may or may not be the cognate receptor of the original HBGF, i.e. the synthetic HBGF analog may additionally or solely bind to the receptor of a different HBGF.

The region W of the foregoing formulas of synthetic HBGF analogs is a synthetic peptide chain that binds an HBGFR and is different from the region X. Region X or W can, for example, each independently have any amino acid sequence that binds an HBGFR, and can include amino acid sequences that are identical to a portion of the amino acid sequence of a HBGF. Alternatively, X or W can each independently have an amino acid sequence homologous rather than identical to the amino acid sequence of an HBGF. The particular HBGFR bound by the synthetic HBGF analog of the invention may or may not be the cognate receptor of the original HBGF, i.e. the synthetic HBGF analog may additionally or solely bind to the receptor of a different HBGF.

The term 'homologous', as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

Particularly useful amino acid sequences as X or W regions include homologs of fragments of naturally occurring HBGFs that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another of the same acidic or basic character.

In another alternative, the X or W region of the synthetic HBGF analog can include an amino acid sequence that shows no detectable homology to the amino acid sequence of any HBGF. Peptides or growth factor analogs useful as components of the X or W region of the synthetic analogs of the present invention, that have little or no amino acid sequence homology with the cognate growth factor and yet bind HBGFRs may be obtained by any of a wide range of methods, including for instance, selection by phage display. See as an example: Sidhu et al. Phage display for selection of novel binding peptides. *Methods Enzymol.* 328:333-63 (2000).

The X or W region of the synthetic HBGF analogs can have any length that includes an amino acid sequence that effectively binds an HBGFR. Preferably, the X or W regions of the synthetic HBGF analogs have a minimum length of at least approximately three amino acid residues. More preferably, the X or W regions of the synthetic HBGF analogs have a minimum length of at least approximately six amino acid residues. Most preferably the X or W regions of the synthetic HBGF analogs have a minimum length of at least approximately ten amino acid residues. The X or W regions of the synthetic HBGF analogs of the invention preferably also have a maximum length of up to approximately fifty amino acid residues, more preferably a maximum length of up to approximately forty amino acid residues, and most preferably a maximum length of up to approximately thirty amino acid residues. In one embodiment of the synthetic HBGF analogs that include two X or W regions, the X or W regions are covalently cross-linked. Suitable cross links can be formed by S—S bridges of cysteines linking the two X or W regions. Alternatively, the cross link can be conveniently formed during simultaneous and parallel peptide synthesis of the X or W region amino acids chains by incorporating a lanthionine (thio-dialanine) residue to link the two identical X chains at alanine residues that are covalently bonded together by a thioether bond. In another method the two X or W region amino acid chains can be cross-linked by introducing a cross-linking agent, such as a dicarboxylic acid, e.g. suberic acid (octanedioic acid), or the like, thereby introducing a hydrocarbon bridge between the two identical X or W regions having a free amino, hydroxyl or thiol group. The cross-linked X or W regions can constitute a cyclic peptide, such as where the terminal amino acids of X are cross-linked through reactive side chains or the terminal groups, optionally with a bridge or other link. An X or W region and a W region may be similarly cross-linked.

In the synthetic HBGF analogs, the Y region of the foregoing formulas may be a linker that is hydrophobic, such as sufficiently hydrophobic to non-covalently bind the HBGF analog to a surface, including a polymeric or metal surface. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethylene-co-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the HBGF analogs to the hydrophobic surface is of sufficient quantity to be detected by an analytical method such as an enzyme-linked immunoassay or a biological assay.

The Y region of the foregoing formulas can include a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids).

The chain of atoms of the Y region can, in certain of the foregoing formulas, be attached to $R_1$ or $R_2$ and to peptide Z. Similarly the chain of atoms of the Y region of certain of the foregoing formulas can be covalently attached to $J_1$ or $J_2$ and to peptide Z. The covalent bonds can be, for example, peptide, amide or ester bonds. Preferably, the Y region includes a chain of a minimum of about nine atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

The amino acid sequence of the Y region is preferably an artificial sequence, i.e. it does not include any amino acid sequence of four or more amino acid residues found in a natural ligand of a HBGF.

In a particular embodiment, the Y region includes a hydrophobic amino acid residue, or a chain of hydrophobic amino acid residues. The Y region can, for example, include one or more aminohexanoic acid residues, such as one, two, three or more aminohexanoic acid residues.

In another particular embodiment, the Y region of the molecule can include a hydrophobic branched or unbranched, saturated or unsaturated alkyl chain of between one and about twenty carbon atoms. In a further embodiment, the Y region can include a chain of hydrophobic residues, such as for instance, ethylene glycol residues. For instance, the Y region can include at least about three, or at least about four, or at least about five ethylene glycol residues. Alternatively, the Y region can include up to about twelve, up to about fifteen, or up to about seventeen ethylene glycol residues. In another alternative embodiment, the Y region can include a combination of amino acid hydrophobic residues.

The Z region of the foregoing formulas is a heparin-binding region and can include one or more heparin-binding motifs, BBxB or BBBxxB as described by Verrecchio et al. *J. Biol. Chem.* 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:1), designating the first three amino acids as each independently selected from lysine or arginine, followed by any two amino acids and a sixth amino acid which is lysine or arginine.

The number of heparin binding motifs is variable. For instance, the Z region may include at least one, at least two, at least three or at least five heparin-binding motifs. Where there are more than one heparin-binding motifs, the motifs may be the same or different. Alternatively, the Z region includes up to a maximum of about ten heparin-binding motifs. In another alternative embodiment, the Z region includes at least four, at least six or at least eight amino acid residues. Further, in certain embodiments the Z region includes up to about twenty, up to about, twenty-five, or up to about thirty amino acid residues. It is to be realized that, in part, the avidity of the Z region for heparin is determined by the particular heparin-binding motifs selected and the number of such motifs in Z. Thus for particular applications both the selection and number of such motifs may be varied to provide optimal heparin binding of the Z region.

In a preferred embodiment, the amino acid sequence of the Z region is RKRKLERIAR (SEQ ID NO:2). In another embodiment, the amino acid sequence of the Z region is RKRKLGRIAR (SEQ ID NO:3). In yet another embodiment, the amino acid sequence of the Z region is RKRKLWRARA (SEQ ID NO:4). In yet another embodiment, the amino acid sequence of the Z region is RKRLDRIAR (SEQ ID NO:5). In yet another embodiment, the amino acid sequence of the Z region is RKRKLERIARC (SEQ ID NO:6). The presence of a terminal cysteine residue optionally affords the opportunity to link other molecules, including detection reagents such as fluorochromes, radioisotopes and other detectable markers, to the Z region, as well as the opportunity to link toxins, immunogens and the like.

Heparin-binding domains that bear little or no sequence homology to known heparin-binding domains are also contemplated in the present invention. As used herein the term "heparin-binding" means binding to the $-NHSO_3^-$ and sulfate-modified polysaccharide, heparin, and also binding to the related modified polysaccharide, heparan sulfate, as well as glycosaminoglycans or proteoglycans containing heparin or heparin sulfate, as well as degradation products of the aforementioned, and synthetic polysaccharides that exhibit heparin-like activity.

The Z region of the synthetic HBGF analogs of the present invention confers the property of binding to heparin in low salt concentrations, up to about 0.15 M NaCl, optionally up to about 1.0 M NaCl, forming a complex between heparin and the Z region of the factor analog. The complex can be dissociated in high concentrations of salts typically greater than 1 M NaCl to release the synthetic HBGF analog from the heparin complex.

The Z region is a non-signaling peptide relative to the HBGFR. Accordingly, when used alone the Z region binds to heparin which can be bound to a receptor of a HBGF, but the binding of the Z region peptide alone does not initiate or block signaling by the receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group. In one embodiment the C terminus of the Z region is an amidated arginine.

As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

"Heparin" as used herein includes heparin, low-molecular-weight variants thereof, or fragments thereof, or any of a number of compounds that bind growth factors in a manner similar to heparin. Such compounds include but are not limited to heparan sulfate, chondroitin sulfate, hyaluronic acid, dextran sulfate, carboxymethyl cellulose, or any of a number of synthetic heparin-mimicking polyanionic compounds. "Heparin" also includes but is not limited to molecules including a mixture of variably sulfated polysaccharide chains composed of repeating units of d-glucosamine and either l-iduronic or d-glucuronic acids, salts of any of the foregoing and derivatives of any of the foregoing. For example, conventional salts of heparin include sodium heparin, calcium heparin, magnesium heparin, and potassium heparin. Heparin derivatives include, but are not limited to ammonium heparin, benzalkonium heparin, and the like. Heparin further includes silyl-heparin compositions as described in U.S. patent application Ser. No. 10/450,309, which is U.S. Patent Application Publication No. 2004/0161442 A1, entitled "Bioactive Coating Compositions and Methods", to Paul O. Zamora, et al., filed on Jan. 28, 2003, the specification of which is hereby incorporated by reference.

FGF Synthetic Analogs

In another particular aspect, the invention provides a synthetic FGF peptide analog used in a coating or method of coating of the invention. The synthetic FGF analogs represented by any of the foregoing formulas, wherein X, or W if it is provided, is an FGF analog which can be any FGF, such as any of the known FGFs, including all 23 FGFs from FGF-1 to FGF-23.

The X or W region of the molecule of formulas of the present invention can include an amino acid sequences found in an FGF, such as for instance FGF-2 or FGF-7. Alternatively, the X or W regions can include sequences not found in the natural ligand of the FGFR bound by the molecule.

The X or W region of synthetic FGF peptide analogs can include an amino acid sequence that is 100% identical to an amino acid sequence found in a fibroblast growth factor or an amino acid sequence homologous to the amino acid sequence of a fibroblast growth factor. For instance, the X or W region can include an amino acid sequence that is at least about 50%, at least about 75%, or at least about 90% homologous to an amino acid sequence from a fibroblast growth factor. The fibroblast growth factor can be any fibroblast growth factor, including any of the known or yet to be identified fibroblast growth factors.

In a particular embodiment, the synthetic FGF analog of the invention is an agonist of the HBGFR. When bound to the HBGFR, the synthetic HBGF analog initiates a signal by the HBGFR.

In a further particular embodiment, the synthetic FGF analog of the invention is an antagonist of the HBGFR. When bound to the HBGFR, the synthetic HBGF analog blocks signaling by the HBGFR.

In another particular embodiment of the present invention, the synthetic FGF analog is an analog of FGF-2 (also known as basic FGF, or bFGF). In another particular embodiment of the present invention, the binding of the synthetic FGF analog to an FGF receptor initiates a signal by the FGF receptor. In a further particular embodiment, the binding of the synthetic FGF analog to the FGF receptor blocks signaling by the FGF receptor.

In a yet further particular embodiment, the present invention provides a synthetic FGF analog of FGF-2. In another particular embodiment, the present invention provides a synthetic FGF analog of FGF-2, wherein the amino acid sequence of the X or W region is YRSRKYSSWYVALKR (SEQ ID NO:7) from FGF-2. In yet another particular embodiment, the present invention provides a synthetic FGF analog wherein the amino acid sequence of the X or W region is NRFHSWDCIKTWASDTFVLVCYDDGSEA (SEQ ID NO:8). In yet another particular embodiment, the present invention provides a synthetic FGF-2 analog wherein the amino acid sequence of the X or W region is HIKLQLQAEERGVVS (SEQ ID NO:9).

In a yet further particular embodiment, the invention provides a synthetic FGF analog of FGF-1, wherein the X or W region is YISKKHAEKNWFVGLKK (SEQ ID NO:10). This sequence is derived from amino acids bridging the beta 9 and beta 10 loop of FGF-1. In yet another particular embodiment, an FGF-1 analog is provided wherein the X or W region is HIQLQLSAESVGEVY (SEQ ID NO:11), corresponding to amino acids derived from the β-4 and β-5 region of FGF-1.

In a yet further particular embodiment, the invention provides a synthetic FGF analog of FGF-7, wherein the X or W region is YASAKWTHNGGEMFVALNQK (SEQ ID NO:12). In yet another embodiment of a synthetic FGF analog of FGF-7, the X or W region is the amino acid sequence YNIMEIRTVAVGIVA (SEQ ID NO:13).

Other FGF receptor binding domains, derived largely from targeting sequences in the C-terminus of human FGF, include the following sequences shown in Table 1:

TABLE 1

| CYTOKINE | PREFERRED X OR W RECEPTOR BINDING DOMAIN | |
|---|---|---|
| FGF-10 | YASFNWQHNGRQMYVALNQK | (SEQ ID NO: 14) |
| FGF-22 | YASQRWRRRGQPNLALDRR | (SEQ ID NO: 15) |
| FGF-9 | YSSNLYKHVDTGRRYYVALNK | (SEQ ID NO: 16) |
| FGF-16 | YASTLYKHSDSERQYVALNK | (SEQ ID NO: 17) |
| FGF-20 | YSSNIYKHGDTGRRFVALNK | (SEQ ID NO: 18) |
| FGF-4 | YESYKYPGMFIALSKN | (SEQ ID NO: 19) |
| FGF-6 | YESDLYQGTYILSKYGR | (SEQ ID NO: 20) |
| FGF-12 | YSSTLYRQQESGRAWFLGNK | (SEQ ID NO: 21) |
| FGF-14 | YSSMLYRQQESGRAWFLGLNK | (SEQ ID NO: 22) |
| FGF-13 | YSSMIYRQQQSGRGWYLGLNK | (SEQ ID NO: 23) |
| FGF-11 | YASALYRQRRSGRAWYLDK | (SEQ ID NO: 24) |
| FGF-1 | SNGGHFLRIL | (SEQ ID NO: 25) |
| FGF-2 | KNGGFFLRIH | (SEQ ID NO: 26) |
| FGF-7 | RTQWYLRID | (SEQ ID NO: 27) |
| FGF-10 | FTKYLKIE | (SEQ ID NO: 28) |
| FGF-22 | STHFFLRVD | (SEQ ID NO: 29) |
| FGF-9 | RTGFHLEIF | (SEQ ID NO: 30) |
| FGF-16 | RTGFHLEIF | (SEQ ID NO: 31) |
| FGF-20 | RTGFHLQIL | (SEQ ID NO: 32) |
| FGF-4 | NVGIGFHLQAL | (SEQ ID NO: 33) |
| FGF-6 | NVGIGFHLQAL | (SEQ ID NO: 34) |
| FGF-12 | QQGYFLQMH | (SEQ ID NO: 35) |
| FGF-14 | RQGYYLQMH | (SEQ ID NO: 36) |
| FGF-13 | RQGYHLQLQ | (SEQ ID NO: 37) |
| FGF-11 | RQGFYLQAN | (SEQ ID NO: 38) |
| FGF-8 | RTSGKHVQVL | (SEQ ID NO: 39) |
| FGF-17 | RTSGKHVQVT | (SEQ ID NO: 40) |
| FGF-18 | RTSGKHIQVL | (SEQ ID NO: 41) |
| FGF-3 | QTKYHLQLH | (SEQ ID NO: 42) |
| FGF-5 | RVGIGFHLQIY | (SEQ ID NO: 43) |
| FGF-19 | SGPHGLSSCFLRIR | (SEQ ID NO: 44) |

TABLE 1-continued

| CYTOKINE | PREFERRED X OR W RECEPTOR BINDING DOMAIN | |
|---|---|---|
| FGF-21 | DDAQQTEAHLEIR | (SEQ ID NO: 45) |
| FGF-23 | ATARNSYHLQIH | (SEQ ID NO: 46) |

TGF-β and BMP Synthetic Analogs

In another particular aspect, the invention utilizes a synthetic BMP peptide analog. The synthetic bone morphogenic protein analogs include embodiments wherein the X or W region includes the amino acid sequence LYVDFSDVGWNDW (SEQ ID NO:47), AISMLYLDENEKVVL (SEQ ID NO:48), ISMLYLDENEKVVLKNY (SEQ ID NO:49), EKVVLKNYQDMVVEG (SEQ ID NO:50), LVVKENEDLYLMSIAC (SEQ ID NO:51), AFYCHGECPFPLADHL (SEQ ID NO:52), PFPLADHLNSTNHAIVQTLVNSV (SEQ ID NO:53), TQLNAISVLYFDDSSNVILKKYRNMVV (SEQ ID NO:54) and/or HELYVSFRDLGWQDWIAPEGYAAY (SEQ ID NO:55).

Alternatively, in another particular aspect the invention provides synthetic Avinin A, the synthetic Avinin A protein analogs include embodiments wherein the X region includes the amino acid sequence MLYYDDGQNIIKK (SEQ ID NO:56) KKIINQGDDYYLMS (SEQ ID NO:57), and/or MLYYDDGQNIIKKDI (SEQ ID NO:58).

Alternatively, in another particular aspect the invention provides synthetic BMP or TGF peptide analogs as shown in Table 2 wherein the transforming growth factor family member peptides are particularly useful in augmenting the activity of endogenous or artificial BMP peptides or TGF peptides, wherein is shown (under the heading "preferred receptor binding domain") the sequence forming all or part of the X or W region of constructs of any of the foregoing formulas.

TABLE 2

| CYTOKINE | PREFERRED X OR W RECEPTOR BINDING DOMAIN | |
|---|---|---|
| TGF-β1 | IVYYVGRKPKVEQLSNMIVRS | (SEQ ID NO: 59) |
| TGF-β2 | TILYYIGKTPKIEQLSNMIVKS | (SEQ ID NO: 60) |
| TGF-β3 | LTILYYVGRTPKVEQLSNMVV | (SEQ ID NO: 61) |
| BMP-2 | AISMLYLDENEKVVLKNYQDMVV | (SEQ ID NO: 62) |
| BMP-3 | SSLSILFFDENKNVVLKVYPNMTV | (SEQ ID NO: 63) |
| BMP-3β | NSLGVLFLDENRNVVLKVYPNMSV | (SEQ ID NO: 64) |
| BMP-4 | AISMLYLDEYDKVVLKNYQEMVV | (SEQ ID NO: 65) |
| BMP-5 | AISVLYFDDSSNVILKKYRNMVV | (SEQ ID NO: 66) |
| BMP-6 | AISVLYFDDNSNVILKKYRNMVV | (SEQ ID NO: 67) |
| BMP-7 | AISVLYFDDSSNVILKKYRNMVV | (SEQ ID NO: 68) |
| BMP-8 | ATSVLYYDSSNNVILRKARNMVV | (SEQ ID NO: 69) |
| BMP-9 | ISVLYKDDMGVPTLKYHYEGMSV | (SEQ ID NO: 70) |
| BMP-10 | ISILYLDKGVVTYKFKYEGMAV | (SEQ ID NO: 71) |
| BMP-11 | INMLYFNDKQQIIYGKIPGMVV | (SEQ ID NO: 72) |
| BMP-12 | ISILYIDAANNVVYKQYEDMVV | (SEQ ID NO: 73) |

TABLE 2-continued

| CYTOKINE | PREFERRED X OR W RECEPTOR BINDING DOMAIN | |
|---|---|---|
| BMP-13 | ISILYIDAGNNVVYKQYEDMVV | (SEQ ID NO: 74) |
| BMP-14 | ISILFIDSANNVVYKQYEDMVV | (SEQ ID NO: 75) |
| BMP-15 | ISVLMIEANGSILYKEYEGMIA | (SEQ ID NO: 76) |

PDGF Synthetic Analogs

In another particular aspect, the invention utilizes a synthetic PDGF peptide analog. The synthetic bone morphogenic peptide analogs include embodiments wherein the X or W region includes the amino acid sequences VRKIEIVRKK (SEQ ID NO:77), KTRTEVFEISRRLIDRTNANFLVW (SEQ ID NO:78), and/or QVRKIEIVRKKPIFKK (SEQ ID NO:79).

Reverse Sequence X or W Regions

It has surprisingly and advantageously been found that in the compounds of the present invention, including those of foregoing formulas, the X or W region may be synthesized in a reverse direction, such that considering the sequence AISM-LYLDENEKVVL (SEQ ID NO:48) illustrated in the conventional N→C orientation, and using formula I, the first amino acid bound to either the $R_1$ side chain or N-terminus amine is the N-terminus amino acid residue (bound through its carboxyl group thereby forming a peptide bond), the second amino acid bound to the N-terminus amino acid residue is the 2 position residue, and so on, and the compounds nonetheless retain biological activity and specifically bind to a BMP receptor. It may be seen that such a construct has, based on a conventional N→C orientation, a reverse sequence, in that it is the carboxyl group of the conventional N-terminus amino acid residue that forms a peptide bond with an amine of $R_1$ where $R_1$ is a diamine amino acid. Thus again employing a conventional N→C orientation, the foregoing sequences may be employed in a reverse orientation, and the resulting compound of present invention is biologically active and may be employed as described herein. According to a preferred embodiment, the X or W region is the sequence LVVKENEDLYLMSIA (SEQ ID NO:80) (again considering the sequence in the conventional N→C orientation.

Other reverse sequences that may be employed, in whole or in part, including homologs thereto, in addition to LVVKENEDLYLMSIA (SEQ ID NO:80), include but are not limited to YNKLVVKENEDLYLMSI (SEQ ID NO:81), KKLIVNSSEDFYL (SEQ ID NO:82), WDNWGVDSFD-VYL (SEQ ID NO:83), GEVVMDQYNKLVVKE (SEQ ID NO:84), LHDALPFPCEGHCYFA (SEQ ID NO:85), VSN-VLTQVIAHNTSNLHDALPFP (SEQ ID NO:86), and LVVKENEDLYLMSIAC (SEQ ID NO:87).

Reverse sequences may similarly be employed, in whole or in part, including homologs thereto, that are reverse sequences of FGF or other HBGF analogs. Thus a reverse sequence of SEQ ID NO:8 may be employed, which is the sequence AESGDDYCVLVFTDSAWTKICDWSHFRN (SEQ ID NO:88). Similarly, a reverse sequence of SEQ ID NO:7 may be employed, which is the sequence RKLAVY-WSSYKRSRY (SEQ ID NO:89). A reverse sequence of SEQ ID NO:10 may also be employed, which is the sequence KKLGVFWNKEAHKKSIY (SEQ ID NO:90). A reverse sequence of SEQ ID NO:11 may also be employed, which is the sequence YVEGVESASLQLQIH (SEQ ID NO:91). A reverse sequence of SEQ ID NO:12 may also be employed, which is the sequence KQNLAVFMEGGNHTWKASAY (SEQ ID NO:92). A reverse sequence of SEQ ID NO:13 may also be employed, which is the sequence AVIGVAVTRI-EMINY (SEQ ID NO:93).

Methods of Synthesizing the Heparin-Binding Growth Factor Analogs

The synthesis of the analogs of the invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The analogs of the present invention can be produced by stepwise synthesis or by synthesis of a series of fragments that can be coupled by similar well known techniques. See, for instance, Nyfeler, Peptide synthesis via fragment condensation. *Methods Mol. Biol.* 35:303-16 (1994); and Merrifield, Concept and early development of solid-phase peptide synthesis. *Methods in Enzymol.* 289:3-13 (1997). These methods are routinely used for the preparation of individual peptides. It is possible to assemble the analogs of the present invention in component parts, such as peptides constituting the X, W, Y and Z components thereof, and to thereafter couple such component parts to assemble the analog. See, for instance, Dawson and Kent, Synthesis of native proteins by chemical ligation. *Annu. Rev. Biochem.* 69:923-960 (2000); and Eom et al., Tandem ligation of multipartite peptides with cell-permeable activity. *J. Am. Chem. Soc.* 125:73-82 (2003).

Advantageously, in the case where the analogs of any of the foregoing formulas of the invention include two identical X region amino acid sequences, the synthesis of these identical X region peptides may be performed in parallel. By this method each cycle of addition adds an amino acid to both of the X region peptides, greatly facilitating the synthesis of these branched molecules.

Peptide libraries that can be used to screen for a desired property, such as binding to an HBGFR can be prepared by adaptations of these methods. See for instance, Fox, Multiple peptide synthesis, *Mol. Biotechnol.* 3:249-58 (1995); and Wade and Tregear, Solid phase peptide synthesis: recent advances and applications. *Austral. Biotechnol.* 3:332-6 (1993).

In a particular embodiment, the synthetic HBGF analog of the invention is an agonist of the HBGFR. When bound to the HBGFR, the synthetic HBGF analog initiates a signal by the HBGFR.

In another particular embodiment, the synthetic HBGF analog of the invention is an antagonist of the HBGFR. When bound to the HBGFR, the synthetic HBGF analog blocks signaling by the HBGFR.

In a particular aspect, the invention provides a method for stimulating growth factor receptor signaling in a cell by contacting the cell with an effective amount of a synthetic HBGF analog according to the foregoing formulas. The effective amount can be readily determined by one of skill in the art. The signaling can result in cytokine release from the cell, stimulation or inhibition of proliferation or differentiation of the cell, chemotaxis of the cell, stimulation or inhibition of the immune system of the mammal.

The present invention thus provides formulations, methods and kits for use of synthetic, bioactive receptor targeting peptides. In one preferred embodiment, the invention relates to formulations, methods and kits for treatment of bone fractures, lesions, and for enhanced bone repair resulting from a) the augmentation of BMP-2 found in demineralized bone matrix (DBM) and bone graft materials, and b) augmentation of host BMP-2 known to be upregulated in bone-repair. In another preferred embodiment, formulations, methods and kits of the present invention are supplied in concert with osteoconductive materials such as tricalcium phosphate, wherein the formulations augment host or exogenous BMP-2 and lead to osteoinduction and increased cellular migration into the bone fill material. In one embodiment, the synthetic, bioactive receptor targeting peptides are of any of formulas I to XIV wherein the X, and if provided, W, regions comprise the sequences of any of SEQ ID NO:25 through SEQ ID NO:49, inclusive, or the reverse sequence thereof. Such compounds are collectively referred to herein as "BMP Growth Factor Analogs."

In another preferred embodiment, the invention relates to formulations, methods and kits to stimulate tissue repair, and specifically cartilage repair, and including repair of dermal wounds, cartilage, bone fractures, and tendons, such repair resulting from the augmentation of endogenous or exogenous FGF, such as augmentation of host FGF known to be upregulated in repair. In another preferred embodiment, formulations, methods and kits of the present invention are supplied in concert with osteoconductive materials such as tricalcium phosphate or other calcium salts, wherein the formulations augment host FGF and leads to osteoinduction and increased cellular migration into the bone fill material. In one embodiment, the synthetic, bioactive receptor targeting peptides are of any of formulas I to XIV wherein the X, and if provided, W, regions comprise the sequences of any of SEQ ID NO:7 through SEQ ID NO:24, inclusive, or the reverse sequence thereof. Such compounds, formulas and claims are incorporated here by reference, and are collectively referred to herein as "FGF Growth Factor Analogs."

In a preferred embodiment, the FGF Growth Factor Analogs employed in the present invention are agonists of basic fibroblast growth factor (bFGF which is also sometimes called FGF-2), increase proliferation of mesenchymal cells including endothelial cells, and bind to FGF receptors and cause signal transduction via same pathway as FGF-2. The FGF Growth Factor Analogs are preferably made by synthetic peptide chemistry methods, and not by recombinant technologies.

In one embodiment, an FGF Growth Factor Analog or a BMP Growth Factor Analog is employed in a composition of the present invention for the treatment of fresh fractures. The composition is injectable using an 18 gauge needle for percutaneous delivery. Thus the composition is biocompatible. In one embodiment, the composition is radiopaque, thereby permitting injecting monitoring by visualization means, such as fluoroscopy. The composition may be radiopaque because one or constituents, such as a calcium compound, is radiopaque, or may be radiopaque because one or compounds, such as a boron compound, are added such that the resulting composition is radiopaque.

In a preferred embodiment, the composition of the present invention is either liquid or a gel, and if a gel may be a thermo-sensitive gel. The composition of the present invention may further include particles, and in one embodiment includes a combination of particles and gel. The composition of the present invention may be formulated such that the FGF Growth Factor Analogs or BMP Growth Factor Analogs are released in vivo over a determined time, selected such that blood clearance is not excessively rapid, but not so slow as to require high concentrations.

For treatment of fractures, including fresh fractures, in one embodiment the composition of the present invention includes carboxymethylcellulose or other complex polysaccharide (Edwards et al., *J Bone Joint Surg.* 86A, 1425-1438, 2004), block copolymers, gelatin or crosslinked gelatin (Kawaguchi et al. *J Clin Endocrinol Metab.* 2001; 86:875-80), a collagen gel, a composition of hyaluronic acid and heparin (Liu et al. J *Biomed Mater Res* 62: 128-135, 2002), a fibrin sealant, one or more mimics of a naturally occurring BMP or FGF, including recombinantly produced BMP or FGF, or a combination of any of the foregoing.

For use as a graft material, in one embodiment the composition of the present invention includes a BMP Growth Factor Analog or an FGF Growth Factor Analog together with a calcium-containing agent, such as for example calcium phosphate or tricalcium phosphate or a combination thereof (Edwards et al., *J Bone Joint Surg.* 2004; 86A: 1425-1438), calcium hydoxyapatite (Ohura K, *J Biomed Mater Res.* 1999; 44: 168-75), calcium sulfate, calcium sulfate dihydrate, demineralized bone matrix (DBM) (Lu and Rabie, Archives of Oral Biology 2002; 47:831-841), blends of calcium-containing materials, or a combination of any of the foregoing. The composition may further include polylactide microbeads. The composition may further include one or more mimics of a naturally occurring BMP or FGF, including recombinantly produced BMP or FGF.

Figure 2:
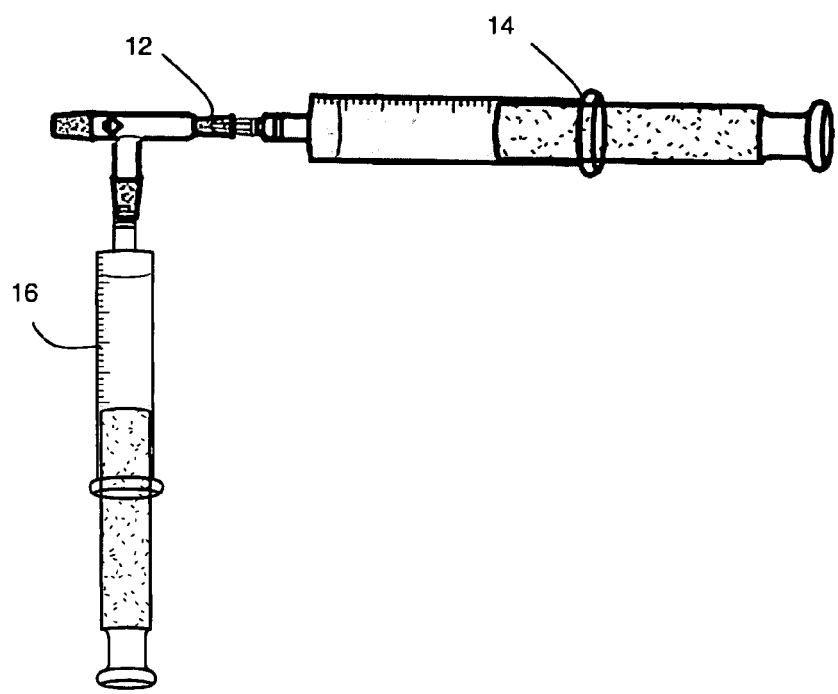
Figure 3:
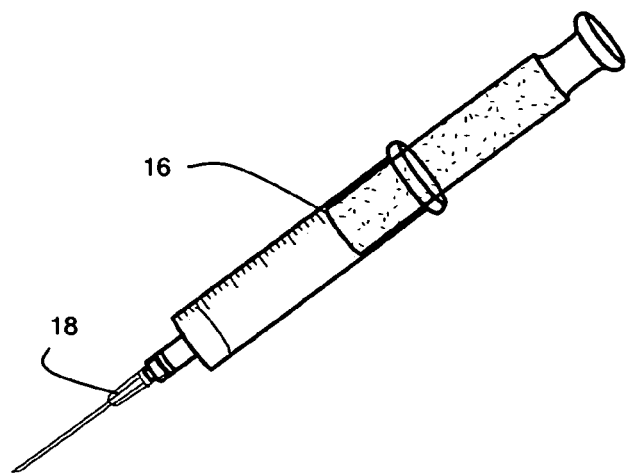
Figure 4:
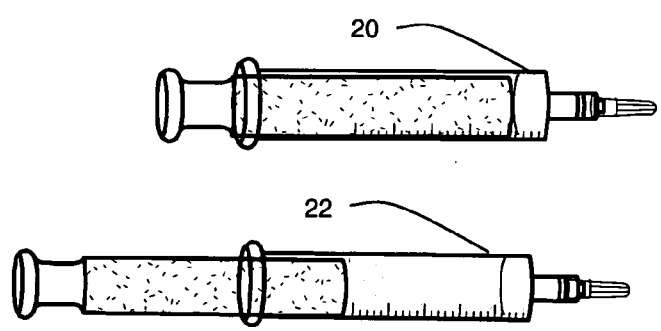
FIGS. 4, 5 and 6 are views of aspects of a kit of the present invention, including a first syringe containing a synthetic heparin-binding growth factor analog, a second syringe and a pass-through connector.
Figure 5:
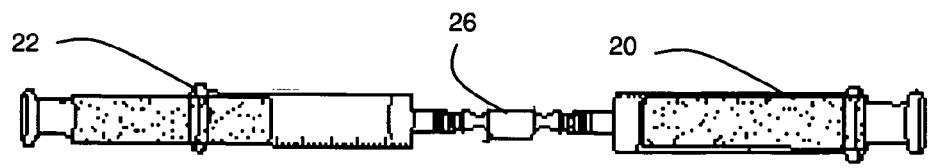
Figure 6:
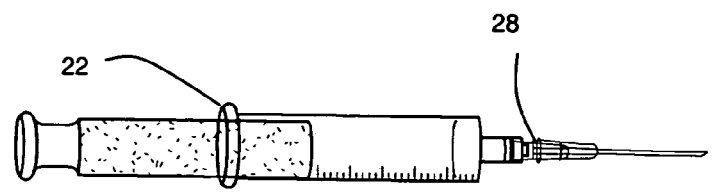

In a preferred aspect, the present invention includes a kit, the kit including a pre-loaded syringe containing a sol of a calcium salt, such as about 2 mL in a 3 cc syringe, and further containing a gelling agent in the pre-loaded syringe, a mixing syringe connector, a vial containing lyophilized BMP Growth Factor Analog or FGF Growth Factor Analog, sterile water or saline for injection (USP), a syringe for dissolving the lyophilized BMP Growth Factor Analog or FGF Growth Factor Analog using the sterile water or saline for injection, a need for injection, preferably for injection via a percutaneous route, such as an 18 gauge need, instructions for use, and other packaging materials. FIG. 1, FIG. 2 and FIG. 3 depict one embodiment of a kit of the present invention, and FIG. 4, FIG. 5 and FIG. 6 depict another embodiment of a kit of the present invention.

In one embodiment, the sol of a calcium salt includes a calcium sulfate sol mixed with a non-ionic polymer (NIP), such as mixed with aqueous 20% NIP. Suitable NIPs include polyethylene glycol 3350 or block copolymers based on ethylene oxide and propylene oxide such as Pluronic F-127 or Pluronic P-85. 2 g of a suitable gelling agent is dissolved in 100 mL of the aqueous NIP solution. Calcium sulfate or other calcium-based material is then added. From about 20 g to about 40 g of calcium-based material is added to 100 g of the gelling solution, such as about 35 g/100 g of gelling solution. The resulting mixture is drawn into individual syringes and capped, and may thereafter be sterilized, and is preferably stored refrigerated until used. Examples of calcium containing agents include anhydrous calcium sulfate, calcium sulfate hemihydrate, calcium sulfate dihydrate, dicalcium phosphate, tricalcium phosphate, tricalcium phosphate, pentacalcium hydroxyl apatite (hydroxyapatite), or tetracalcium phosphate monoxide. The calcium containing agents may be used singly or in combination, and may form sols, suspensions, or be suspensions of aggregates or microparticles. Examples of gelling agents include hydroxypropyl cellulose, carboxymethylcellulose, hydroxypropyl(methyl) cellulose, agar, alginates, hyaluronic acid, heparin, dextran sulfate, gelatin, and collagen.

The lyophilized preparation of BMP Growth Factor Analog or FGF Growth Factor Analog can include the desired concentration of peptide added to an aqueous 10% NIP solution, which is then filter sterilized, such as through a 0.22 micron filter, dispensed into vials, lyophilized and stored refrigerated. Alternatively, the peptide may be lyophilized in a syringe, suitable for direct mixing with the calcium-containing gel. The lyophilized peptide preparation may included any number of additives, including bulking agents such as simple sugars including dextrose, maltose, mannitol, lactose, sucrose, and the like, or polyethylene glycol, or, buffer salts, stabilizers such as amino acids or antioxidants, and surfactants to decrease aggregation and non-specific peptide adsorption. The teachings of U.S. patent application Ser. No. 11/064,039, entitled "Positive Modulator of Bone Morphogenic Protein-2," with respect to pharmaceutical preparations, pharmaceutically acceptable salts, excipients and the like is specifically incorporated as if set forth in full.

Other kit components can be included, including antibiotics such as gentamycin or tobramycin, anesthetics such as lidocane, or metabolic enhancers, such as ascorbic acid or glutamine.

In one embodiment, the calcium-based agent is Coaptite®, a synthetic injectable implant composed of smooth CaHA microspheres with a diameter range of 75 μm to 125 μm and suspended in an aqueous gel carrier, as sold by BioForm Medical, Inc. These consistently shaped and sized particles have proven safe and biocompatible while allowing gradual tissue ingrowth, and may also be employed as a radiopaque marker.

Kit components, other than the lyophilized preparation of BMP Growth Factor Analog or FGF Growth Factor Analog, can be sterilized by any means known in the art, preferably a method such as electron beam (e-beam) sterilization, a quick, low-heat generation method suitable for low profile/low density materials. Other methods can be employed, such as gamma sterilization.

In one embodiment, the kit includes a 3 mL Leur-lok syringe containing 2 mL of carrier, with a Leur-closure and enclosed within a non-breathable aluminum/plastic wrap. A syringe connector is also provided.

Formulations and compositions of the present invention can thus be used to reduce the effective dose of recombinant BMP-2, to maximize the biological activity of biological preparations such as those including demineralized bone matrix (DMB), bone marrow, bone marrow cells, bone chips, or morselized bone, and to augment the endogenous levels of BMP-2 generated by host tissue during bone healing process.

DBM is one alternative material that is bone-derived and widely used in clinical practice. DBM is processed from human bone via solvent and acid treatments, and in its final form contains collagens and low levels of growth factors. DBM is available from a number of companies and organizations, including Wright Medical Technologies, Osteotech, the American Red Cross, and Innova. DBM, via the collagen component, provides a scaffold on which new bone forms and it also has some osteoinductive potential via its low levels of growth factors. It may also elicit some activation of mesenchymal stem cells from the surrounding area that differentiate into osteoblasts. In one embodiment, the formulation of the present invention includes DBM. Other bone-derived materials which may be substituted for DBM include bone marrow, bone marrow cells, autologous bone chips, and morselized bone.

The osteoinductive potential of DBM is low, however, and varies widely from lot-to-lot and manufacturer-to-manufacturer. Since the growth factors in DBM are expected to have their most pronounced effect on osteoprogenitor cells, the availability of osteoprogenitor cells is critical when demineralized bone matrix is used. The limited ability of DBM to elicit a robust osteoinduction is widely seen as a limiting factor in the use of this material.

Among the calcium-rich bone graft materials, there are a large number of commercially available products bone filler agents that are not derived from human sources, including Pro Osteon (coralline hydroxyappatite, Interpore Cross International), Bioglass (bioactive glass implant, US Biomaterials Corp.), Collagraft (hydroxyapatite/tricalcium phosphate and pure bovine fibrillar collagen, Zimmer), Cellplex™ (tricalcium phosphate, synthetic cancellous bone, Wright Medical Technologies, Inc.), and a number of calcium phosphates, calcium phosphate fillers, and calcium sulfates including calcium sulfate hemihydrate and calcium sulfate dihydrate. All of these materials are osteoconductive and support the ingrowth of capillaries, perivascular tissues, and osteoprogenitor cells from a host into an implant or graft. They are not, however, osteoinductive. Any of the calcium-rich bone graft materials may be employed in a composition of the present invention, preferably in combination with a BMP Growth Factor Analog or an FGF Growth Factor Analog.

The formulation, kit and composition of the present invention provides an injectable compound for bone fractures, bone voids, spinal fusion or dental voids, and comprising a minimally invasive, injectable medical device prepared from a kit for the treatment of bone fractures, bone voids, spinal fusion, or dental voids. In one embodiment, the kit comprises a vial containing a sterile, lyophilized preparation of a synthetic growth factor construct, such as a BMP Growth Factor Analog or an FGF Growth Factor Analog, or mixtures thereof, and a pre-filled syringe containing an aseptically prepared sol of calcium sulfate, or alternatively another calcium-containing compound, such as tricalcium phosphate or microparticles of hydroxyapatite.

Thus, in one embodiment the device is composed of microparticles of calcium sulfate complexed with a synthetic growth factor construct and suspended in a thermo-sensitive carrier that undergoes gelation upon injection. Synthetic growth factor constructs that are employed, such as the BMP Growth Factor Analogs, augment the activity of bone morphogenetic protein 2 (BMP-2). Mixing of a portion of the hydrated contents of the BMP Growth Factor Analog vial with contents of the calcium sulfate syringe results in complexation of the synthetic growth factor construct with the microparticles.

In another embodiment, the microparticles a composed of hydroxyapatite particles ranging in size from 10-500 microns and preferably between 50 and 150 microns.

In one embodiment, the prepared injectable for bone fractures has a volume of approximately 3 cc, a calcium sulfate content approaching 23% and a synthetic growth factor construct content of between about 0.05 and about 500 μg/cc.

The prepared injectable of the present invention provides calcium sulfate particles as a tissue in-growth scaffold and a synthetic growth factor construct coating which augments endogenous BMP-2 naturally produced in bone fractures. The injectable can be used for treating lower extremity, closed, bone fractures with adequate blood supply, and preferably for single administration use.

Use of the prepared injectable of the present invention is intended to provide a decreased, time-weighted presence of pain with weight bearing, an increased range of motion and strength (increased "Constant-Score"), a decreased need for arthroscopy-guided/open reduction and internal fixation, and an increase in time-weighted callus formation on X-ray or MRI.

Particularly preferred in the practice of the invention is the FGF Growth Factor Analog herein called "F2A4-K-NS," which has an estimated molecular weight of 5681 and is of formula XIV with the sequence H-YRSRKYSSWY- VALKRK(H-YRSRKYSSWYVALKR)-Ahx-Ahx-Ahx-RKRLDRIAR-NH$_2$, where Ahx is aminohexanoic acid.

Also particularly preferred in the practice of the invention is the BMP Growth Factor Analog herein called "B2A2-K-NS," which has an estimated molecular weight of 5487 and is of formula XIV with the sequence H-LVVKENEDLYLM-SIAK(H-LVVKENEDLYLMSIA)-Ahx-Ahx-Ahx-RKRKLERIAR-NH$_2$, where Ahx is aminohexanoic acid.

Also particularly preferred in the practice of the invention is the PDGF Growth Factor Analog herein called "PBA2-1" and is of formulat XIV with the sequence H-VRKIE-IVRKKK(H-VRKIEIVRKK)-Ahx-Ahx-Ahx-RKRKLER-LAR-NH$_2$, where Ahx is aminohexanoic acid.

In one particular aspect of the invention, there are provided a plurality of formulations which may be employed. The formulations may be present in kit format, such that a growth factor analog, such as a BMP Growth Factor Analog, PDGF Growth Factor Analog, or FGF Growth Factor Analog, is present in one container, which may be a vial, syringe or other storage container, and a calcium-containing agent is contained in a second container, which may similar be a vial, syringe or other storage container. Preferably the calcium-containing agent is a gel, sol, paste or similar miscible substrate, preferably containing one or more polymers, such as a non-ionic polymer, and a gelling agent. In one aspect the components are mixed together prior to patient administration.

The following formulations, and those given in the examples to follow, are exemplary, and other formulations may be employed and are contemplated in the practice of the invention. It may readily be seen that formulations, in general, will contain a synthetic heparin-binding growth factor analog, such as one of any of formulas I to XIV, and a calcium-containing agent. The synthetic heparin-binding growth factor analogs any of formulas I to XIV may contain a Z region as in any of SEQ ID NO:1 to SEQ ID NO:6, and may contain an X or W region, as appropriate, as in any of SEQ ID NO:7 to SEQ ID NO:93. Alternatively, either the Z region or the X or W region, or both, may be other than as disclosed in SEQ ID NO:1 through SEQ ID NO:93. Similarly, either the Z region or the X or W region, or both, may comprise a portion of SEQ ID NO:1 through SEQ ID NO:93, or may be a homolog of all or a portion of SEQ ID NO:1 through SEQ ID NO:93.

First Formulation

In one specific embodiment, a prepared injectable of the present invention is made by preparation of pre-filled syringes. Pluronic F-127 is dissolved in ice-cold water (USP) to affect a 20% solution. This solution is used to dissolve sodium carboxymethylcellulose (CMC). For dissolution, to 2 grams of CMC is added sufficient amounts of the 20% Pluronic F-127 solution to result in a final volume of 100 mL when the CMC is wetted. Complete dissolution of the CMC is affected by autoclaving the solution (121° C., 15 psi, 15 minutes). The autoclaved solution is cooled under refrigeration and the volume of the cool solution adjusted to 100 mL with water (USP), if needed. The result is a sterile aqueous solution that is maintained on wet ice or refrigerated. The resulting sterile solution is then used to hydrate calcium sulfate dihydrate (CaSO$_4$.2H$_2$O). For hydration and using sterile technique and a temperature of approximately 4° C., 35 g of sterile, dry CaSO$_4$ is wetted with sufficient sterile solution to result in a final volume of 100 mL. The final solution is introduced into a large-volume syringe-type plunger and used to fill 3 cc capacity sterile syringes with 2 cc of sol. The filled syringes are then capped with sterile mixing valves, closures applied, and the syringes stored refrigerated.

In one preferred embodiment, the BMP Growth Factor Mimetic B2A2-K-NS is used in the preparation of the lyophilized peptide. The peptide is dissolved in an aqueous solution of 5% dextrose containing 0.05% Pluronic F-127 to a concentration of 60 µg/mL, and sterile filtered through a 0.22 micron filter. The peptide is then dispensed (100 µl) into 2 cc capacity amber vials, slotted grey butyl stoppers placed on the vials, the contents of the vials frozen (–80° C.), and the vials placed in a lyophilizer. The samples are then lyophilized until the pressure stabilizes, typically to near 30 mTorr. The vials are then fully stoppered and closures applied. The vials so prepared are stored frozen or refrigerated.

Second Formulation

In a second specific embodiment, Pluronic F-127 is dissolved in ice-cold water (USP) to provide a 20% solution. This solution is used to dissolve CMC. For dissolution, to 2 grams of CMC are added sufficient amounts of the 20% Pluronic F-127 solution to result in a final volume of 100 mL when the CMC is wetted. Complete dissolution of the CMC is affected by autoclaving the solution (121° C., 15 psi, 15 minutes). The autoclaved solution is cooled under refrigeration and the volume of the cool solution adjusted to 100 mL with water (USP), if needed. The result is a sterile aqueous solution that is maintained on wet ice or refrigerated.

The sterile solution from above is then used to hydrate anhydrous calcium sulfate (CaSO$_4$). For hydration and using sterile technique and a temperature of approximately 4° C., 35 g of sterile, dry CaSO$_4$ is wetted with sufficient sterile solution to result in a final volume of 100 mL. The final solution is introduced into a large-volume syringe-type plunger and used to fill 3 cc capacity sterile syringes with 2 cc of sol. The filled syringes are then capped with sterile mixing valves, closures applied, and the syringes stored refrigerated.

The BMP Growth Factor Analog B2A2-K-NS is used in the preparation of the lyophilized peptide. The peptide is dissolved in an aqueous solution of ice-cold 10% Pluronic F-127 to a concentration of 60 µg/mL, and sterile filtered through a 0.22 micron filter. The peptide is then dispensed (1.5 cc) into 2 cc capacity amber vials, slotted grey butyl stoppers placed on the vials, the contents of the vials frozen (–80° C.), and the vials placed in a lyophilizer. The samples are lyophilized until the pressure stabilizes, typically to near 30 mTorr. The vials are then fully stoppered and closures applied. The vials so prepared are stored frozen or refrigerated.

Third Formulation

Syringes containing calcium sulfate dihydrate as in the First Formulation are prepared and form one component of a formulation kit. The kit is composed of:
  (a) a vial containg a sterile, lyophilized preparation of a BMP Growth Factor Analog such as B2A2-K-NS,
  (b) a pre-filled syringe containing an aseptically prepared aqueous sol of calcium sulfate, and
  (c) a container of demineralized bone matrix.

In this configuration, mixing of the hydrated contents of the B2A2-K-NS vial with contents of the calcium sulfate syringe results in complexation of peptide with the microparticles. This mixture is then mixed with the DBM into a putty-like material for surgical application to bone defects.

Fourth Formulation

Syringes containing calcium sulfate dihydrate as in the First Formulation are prepared and form one component of a formulation kit. The kit is composed of:

(a) a vial containg a sterile, lyophilized preparation of an FGF Growth Factor Analog such as F2A4-K-NS,
(b) a pre-filled syringe containing an aseptically prepared aqueous sol of calcium sulfate, and
(c) a container of demineralized bone matrix.

In this configuration, mixing of the hydrated contents of the F2A4-K-NS vial with contents of the calcium sulfate syringe results in complexation of peptide with the microparticles. This mixture is then mixed with the DBM into a putty-like material for surgical application to bone defects.

Fifth Formulation

Syringes containing calcium sulfate dihyrate as in the First Formulation are prepared and form one component of a formulation kit. The kit is composed of:
(a) a vial containing a lyophilized preparation of B2A2-K-NS plus demineralized bone matrix (DBM), and
(b) a pre-filled syringe containing an aseptically prepared sol of calcium sulfate.

In this configuration, an aqueous solution is added to the vial containing a lyophilized preparation of B2A2-K-NS plus DBM. To the same vial is added the contents of the calcium sulfate syringe and mixed to provide putty-like material for surgical application to bone defects.

Sixth Formulation

Syringes containing calcium sulfate dihyrate as in the First Formulation are prepared and form one component of a formulation kit. The kit is composed of:
(a) a vial containing a lyophilized preparation of F2A4-K-NS plus DBM, and
(b) a pre-filled syringe containing an aseptically prepared sol of calcium sulfate. In this configuration, the contents of the syringe are added to the vial containing a lyophilized preparation of F2A4-K-NS plus DBM and mixed to form putty-like material for surgical application to bone defects.

It may thus be seen that in one embodiment there is provided a kit as illustrated in FIG. 1. Vial 10 contains a growth factor analog, such as a BMP Growth Factor Analog, PDGF Growth Factor Analog, or FGF Growth Factor Analog, which growth factor analog may be conventionally lyophilized, and is made soluble by the addition of water, saline or other aqueous media, or may be in a stable liquid formulation, with such buffers, excipients, and other agents as are appropriate. Syringe 14 is provided as a pre-filled syringe, containing a sol or gel including a calcium-containing agent. In one aspect there is provided a formulation for a sol or gel contained in syringe 14 as provided in any of the foregoing formulations or any examples presented hereafter. The contents of vial 10 may, if lyophilized, be solubilized with an appropriate solvent, such as Sterile Water for Injection (USP). The contents of vial 10 may be withdrawn into an empty syringe, such as syringe 16, which may for example be a 3 cc capacity syringe. Syringe 14 prefilled with a calcium-containing agent, and with three-way valve 12 attached to syringe 14, is removed from refrigeration. Three-way valve 12 is adjusted such that the side port is opened. Excess air can be removed by carefully advancing the gel though the valve such that the gel entered the side port but did not extrude. The needle is removed from syringe 16 containing synthetic heparin-binding growth factor analog peptide and syringe 16 attached to the side port of three-way valve 12 connected to the calcium gel-containing syringe 14. The two solutions are mixed by repeated pushing through valve 12. The solutions are mixed for at least 1 minute with at least 30 passes through valve 12. One syringe, such as for example syringe 16, is then filled with the entire contents of the gel. The valve 12 and empty syringe 14 are detached and discarded. 20-gauge needle 18 is added to syringe 16 containing the mixture of calcium gel and synthetic heparin-binding growth factor analog peptide. The preparation is suitable for injection for bone fractures.

In another embodiment there is provided the kit as shown in FIGS. 4, 5 and 6. Syringe 20 contains a growth factor analog, such as a BMP Growth Factor Analog, PDGF Growth Factor Analog, or FGF Growth Factor Analog, which growth factor analog may be conventionally lyophilized, or may be in a stable liquid formulation, with such buffers, excipients, and other agents as are appropriate. Syringe 22 contains a sol or gel including a calcium-containing agent. In one aspect there is provided a formulation for a sol or gel contained in syringe 22 as provided in any of the foregoing formulations or any examples presented hereafter. Connector 26 may be employed to interconnect syringe 20 and syringe 22, and the contents thereof admixed by repeated passage of materials from one syringe into the other. In this manner the lyophilized growth factor analog preparation in syringe 20 may be solublized by means of the sol or gel in syringe 22. One mixed, the preparation is removed into one syringe, such as syringe 22, and a suitable gauge needle attached thereto, such as needle 28. The preparation is suitable for administration by injection.

The invention is further illustrated by the following non-limiting examples.

EXAMPLE 1

Preparation of Gel Materials for Treating Bone Fractures

Preparation of calcium gel. To a glass beaker containing 400 mL of sterile ice-cold water 100 g of Pluronic F-127 was added slowly with mixing. The solution was mixed overnight at 2-4° C. and the final volume adjusted to 500 mL using with sterile water. 100 mL of the resulting Pluronic F-127 solution was added to an autoclave safe bottle, followed by the addition of 2 g of CMC. The resulting mixture was autoclaved for 15-30 minutes at 15 psi and 121° C., and then chilled, with periodic mixing, in a refrigerator. The volume was adjusted to 100 mL with sterile water, as required. Using a double-barrel syringe type mixer, 45 mL of the resulting Pluronic F-127 and CMC solution was mixed with 10.5 g of calcium sulfate dihydrate until the resulting calcium gel was uniformly dispersed. Using a syringe-type dispenser with a Leur-lok, 3 mL capacity syringes were loaded with 1.5 mL of the calcium gel and sealed with a three-way valve closure system.

Preparation of lyophilized synthetic heparin-binding growth factor analog peptide. A sterile aqueous solution containing 5.5% glucose and 0.1% Pluronic F-127 was prepared. This solution was used to dissolve an appropriate amount of lyophilized synthetic heparin-binding growth factor analog peptide and the resultant solution was filter sterilized. 0.1 mL aliquots of the solution were dispensed into vials and the vial contents frozen and placed in a lyophilization device. The lyophilization process ran for 48 hours, after which the head space gas was purged with a sterile neutral gas, grey butyl rubber stoppers applied to close the vials and aluminum crimps applied.

EXAMPLE 2

Preparation of Paste Materials for Treating Boney Voids or in the Treatment of Spinal Fusion Preparation of calcium paste. 60 g of Pluronic F-127 were weighed out and slowly added to 140 mL of ice cold sterile water in an autoclavable bottle to form a thick Pluronic F-127 paste. The paste was autoclaved as in Example 1 to achieve sterility. As needed, the volume was adjusted to 200 mL and the Pluronic F-127 paste stored under refrigeration.

8 g of CMC was weighed and added to 180 mL of ice cold sterile water in an autoclavable bottle with mixing to form a thick CMC paste. The paste was autoclaved as above, the volume adjusted to 200 mL as needed, and the CMC paste stored under refrigeration.

Calcium sulfate dihydrate was weighed in units of 10.5 g and sterilized by electron beam treatment.

To prepare the paste, 120 mL of ice cold, sterile Pluronic F-127 paste was poured into a sterile container together with 120 mL of the sterile CMC paste. 8 units of 10.5 g each of calcium sulfate dihyrate was added and mixed into a thick calcium paste. The resultant calcium paste was cooled for several hours and then mechanically mixed to insure uniform dispersion. Using a syringe-type dispenser with a Leur-lok, 5 mL capacity syringes were loaded with 4 mL of the calcium paste.

Preparation of lyophilized synthetic heparin-binding growth factor analog peptide. A sterile aqueous solution containing 5.5% glucose and 0.1% Pluronic F-127 was prepared. This solution was used to dissolve an appropriate amount of lyophilized synthetic heparin-binding growth factor analog peptide and the resultant solution was filter sterilized. 0.1 mL aliquots of the solution were dispensed into vials and the vial contents frozen and placed in a lyophilization device. The lyophilization process ran for 48 hours, after which the head space gas was purged with a sterile neutral gas, grey butyl rubber stoppers applied to close the vials and aluminum crimps applied.

EXAMPLE 3

Preparation Of Injectable Gel Suitable For Treating Bone Fractures

A vial containing lyophilized synthetic heparin-binding growth factor analog peptide of Example 1 was removed from storage conditions and the rubber septum wiped with a sterile alcohol swab. A sterile needle was attached to an empty 3 cc capacity Leur-lok syringe and 1.0 mL (1.0 cc) of Sterile Water for Injection (USP) added. The water was injected into the vial containing the lyophilized synthetic heparin-binding growth factor analog peptide and the contents gently mixed to dissolve. 0.5 mL (0.5 cc) of the solution containing synthetic heparin-binding growth factor analog peptide was withdrawn into the empty 3 cc capacity syringe. A syringe with a three-way valve and containing calcium gel of Example 1 was removed from refrigeration. The three-way valve was adjusted such that the side port was opened. Excess air was removed by carefully advancing the gel though the valve such that the gel entered the side port but did not extrude. The needle was removed from the syringe containing synthetic heparin-binding growth factor analog peptide and the syringe attached to the side port of the three-way valve connected to the calcium gel containing syringe. The two solutions were mixed by repeated pushing through the central mixing hub. The solutions were mixed for at least 1 minute with at least 30 passes through the mixing hub. One syringe was then filled with the entire contents of the gel. The mixing hub and empty syringe were detached and discarded. A 20-gauge needle was added to the syringe containing the mixture of calcium gel and synthetic heparin-binding growth factor analog peptide. The preparation was suitable for injection for bone fractures.

EXAMPLE 4

Preparation Of Injectable Paste Suitable For Treating Boney Voids and Inducing Spinal Fusion A vial containing lyophilized synthetic heparin-binding growth factor analog peptide of Example 2 was removed from storage conditions and the rubber septum wiped with a sterile alcohol swab. Using aseptic technique, 0.5 mL of Sterile Water for Injection was added to the vial and the contents gently mixed to dissolve. The contents of the vial were withdrawn into a 5 mL syringe and the needle detached without introducing air. That syringe was attach via a female connecting hub attached to a 5 mL capacity syringe loaded with 4 mL of the calcium paste of Example 2. The two solutions were mixed by repeated pushing through the connecting hub. The solutions were mixed for at least 1 minute with at least 30 passes through the mixing hub. One of the syringes was filled with the entire contents of the paste, and the connecting hub and empty syringe removed and discarded. The resulting paste was suitable for administration.

EXAMPLE 5

Preparation of Injectable Gel Containing Human Demineralized Bone Matrix

An injectable calcium gel was prepared as described in Example 1. The calcium gel was then mixed with human demineralized bone matrix (DBM) such that the final gel contained 250 mg of DBM.

EXAMPLE 6

Use Of Gel And Peptide F2A4-K-NS To Augment DBM-Induced Ectopic Mineralization

DBM was formulated into a calcium gel as in Example 5, and the resulting gel prepared for injection as in Example 3, with one portion containing F2A4-K-NS as the synthetic heparin-binding growth factor analog peptide and the second portion not containing any peptide. Aliquots of each were injected subcutaneously into athymic rats. After 28 days the resultant tissue was excised and fixed. The tissue was then examined with soft X-rays and micro-computerized tomography (micro-CT), and by histological methods including von Kossa staining. Inclusion of F2A4-K-NS with DBM in the injected gel resulted in an increased bone deposition as determined by soft X-ray and micro-CT analysis. DBM-containing tissues showed extensive granular and porous mineralization compared to carrier alone which was poorly mineralized. However, when F2A4-K-NS plus DBM was used the mineralization was both qualitatively and quantitatively the most extensive. Additionally, the highest amount of von Kossa staining for calcium was observed in tissues from animals that had received DBM plus F2A4-K-NS. F2A4-K-NS in amounts of 100 ng per 0.2 mL of injectable DBM gel generated the most optimal results.

Figure 7:
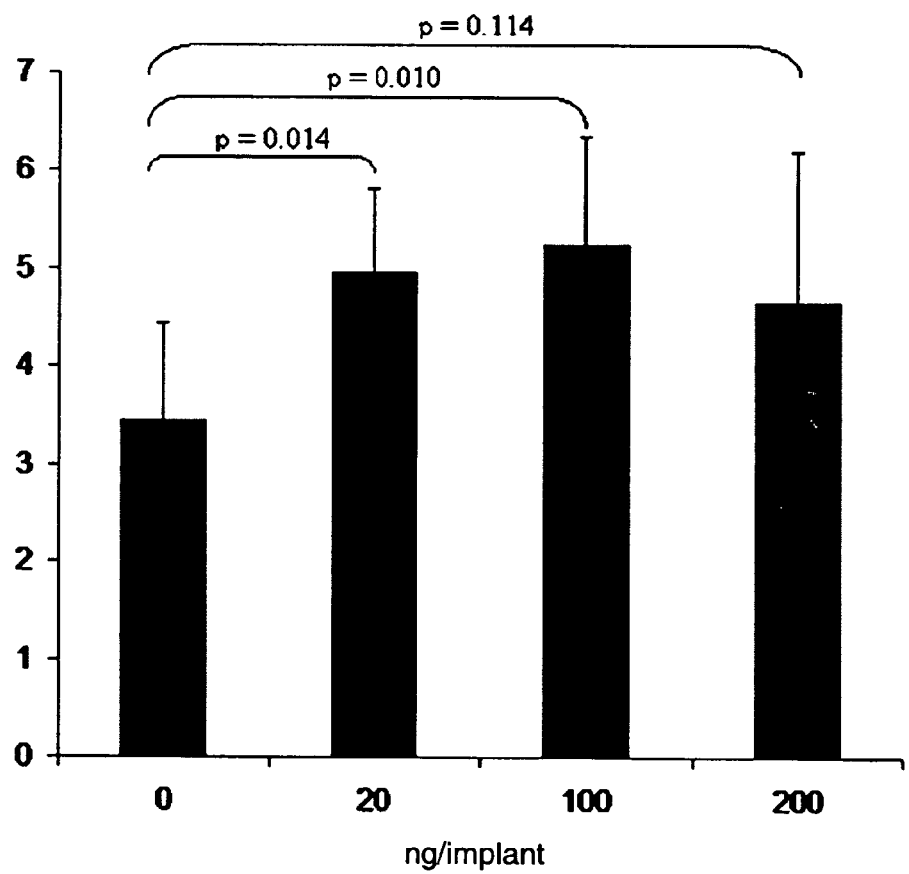
FIG. 7 is a bar chart of densitometry measurements from digitized X-ray images animals administered DBM without F2A4-K-NS and with 20, 200 and 200 ng/implant of F2A4-K-NS.

Densitometry measurements from digitized X-ray images of DBM without F2A4-K-NS and with 20, 200 and 200 ng/implant of F2A4-K-NS are shown in FIG. 7. The DBM-containing tissue samples were collected 4 weeks after implanted and X-rayed using a mammography machine. Data is presented in FIG. 7 as the average pixels above threshold x $10^5$ per region-of-interest (ROI)+standard deviation.

EXAMPLE 7

Figure 8:
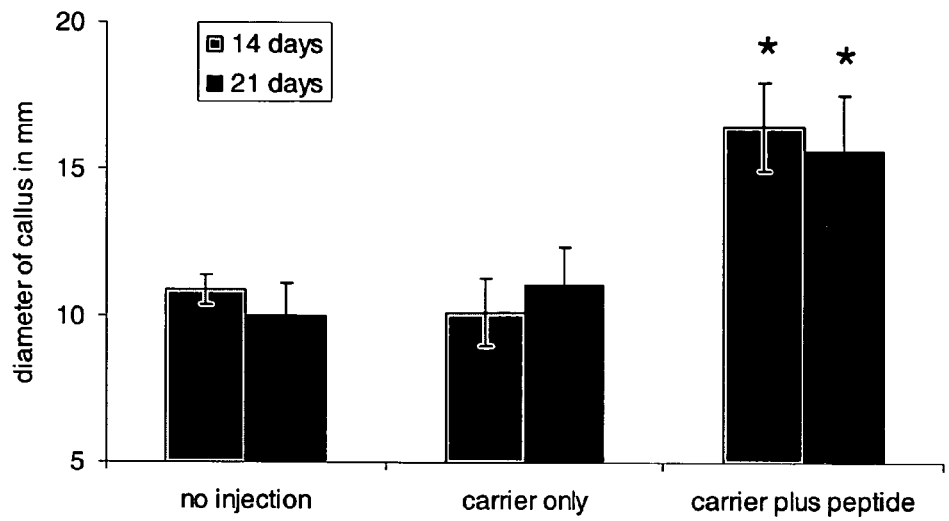
FIG. 8 is a bar chart of callus diameter for fractures injected with calcium gel (carrier) plus B2A2-K-NS (peptide) compared to no injection or carrier only.

Use Of Gel And Peptide B2A2-K-NS To Increase Callus Size in a Rat Tibia Fracture Male Sprague Dawley rats were used to generate closed, transverse fractures of the femur as described in *J. Orthoped. Res.* 2:97-101 (1984). The cross-sectional diameter of the calluses from the fractured rat tibias were measured from radiographs at 14 and 21 days after injection of calcium gel of Example 1 prepared as in Example 3 in which B2A2-K-NS was the synthetic heparin-binding growth factor analog peptide, with calcium gel alone (with no peptide) and no injections serving as controls. The fractures injected with calcium gel plus B2A2-K-NS were significantly (p<0.001) larger than controls at both time points as determined by ANOVA followed by post-hoc Multiple Comparisons versus Control Group (Bonferroni t-test), as shown in FIG. 8.

EXAMPLE 8

Additional Animal Studies

Male athymic rats were employed, with each animal receiving two subcutaneous administrations of 0.2 mL each in a pouch formed by making an incision through the skin and using a hemostat and blunt dissection to make a pouch approximately 5 cm long. The pouches were positioned on the upper flanks on either side of the backbone. After administration by injection into the pouch the surgical site was closed with stainless steel surgical clips.

Material was formulated in an ice cold aqueous carrier containing a final concentration of 20% Pluronic F-127, 2% sodium carboxymethylcellulose (CMC), and 25% calcium sulfate dihydrate, either with or without DBM (375 mg/mL). The gel solutions were mixed in a ratio of 2:1 immediately prior to injection with saline containing either B2A2-K-NS or F2A4-K-NS or containing no peptide, all at the appropriate dilution.

Four experimental arms were used: a) gel solution alone, b) gel solution with DBM, c) gel solution with DBM and B2A2-K-NS, or d) gel solution with DBM and F2A4-K-NS. B2A2-K-NS was used at concentrations resulting in 1, 5, 10, or 20 µg per administration, and F2A4-K-NS was used at concentrations resulting in 20, 100, or 200 ng per administration.

Figure 9:
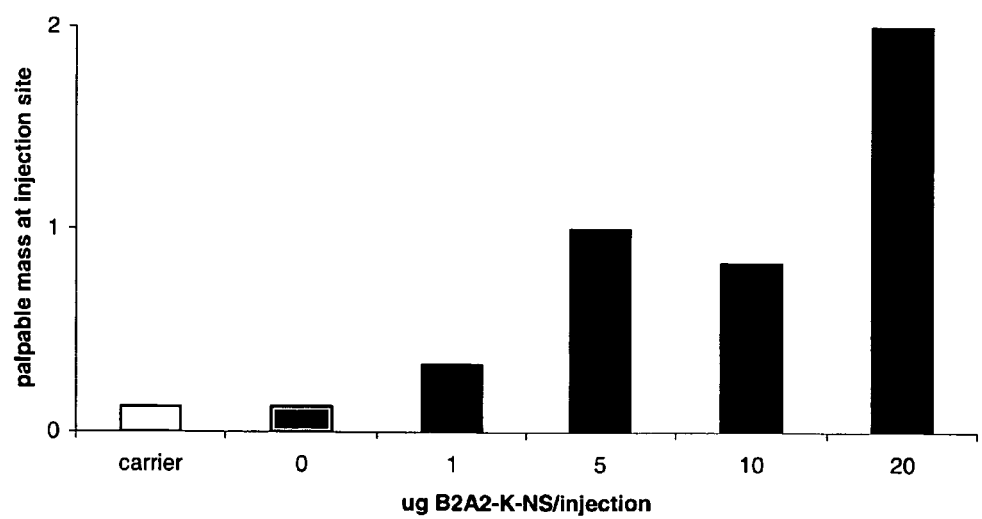
FIG. 9 is a bar chart of scored results of palpable implant materials for different quantities of B2A2-K-NS at two weeks after injection, with injection sites not palpable scored as 0, weakly palpable injection sites scored as 1, and clearly palpable injection sites scored as 2.
Figure 10:
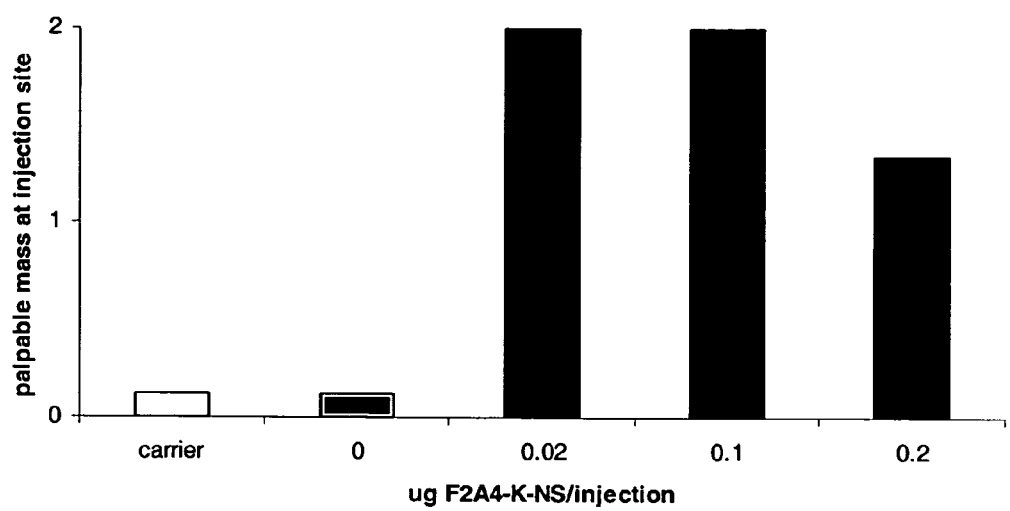
FIG. 10 is a bar chart of scored results of palpable implant materials for different quantities of F2A4-K-NS at two weeks after injection, with injection sites not palpable scored as 0, weakly palpable injection sites scored as 1, and clearly palpable injection sites scored as 2.

At two weeks after injection, the implant materials in animals receiving gel solution alone or gel solution with DBM had regressed and were generally not palpable. Animals receiving gel solution with DBM and B2A2-K-NS or F2A4-K-NS had more frequently palpable implanted materials, with all animals receiving 20 µg B2A2-K-NS per administration having palpable implanted materials. FIGS. 9 and 10 show the scored results of palpable implant materials for different quantities of B2A2-K-NS or F2A4-K-NS at two weeks after injection, with injection sites not palpable scored as 0, weakly palpable injection sites scored as 1, and clearly palpable injection sites scored as 2.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A formulation for bone or cartilage repair, comprising: a synthetic heparin-binding growth factor analog of formula XIII

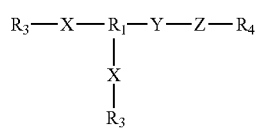

wherein R1 is a diamine amino acid, the diamine amino acid may be an L- or D-diamine amino acid, selected from 2, 3 diamino propionyl amino acid, 2, 4 diamino butylic amino acid, lysine or ornithine;

R3 is a hydrogen (H) such that the terminal group is $NH_2$ or $NH_3^+$;

R4 is $NH_2$, or NH(alkyl);

Y comprises (aminohexanoic acid)$_3$ covalently bonded to $R_1$ and Z;

Z is selected from the group consisting of SEQ ID NO: 2, SEQ ID NO: 3, SEQ ID NO: 4, SEQ ID NO: 5 and SEQ ID NO 6;

X is the same and is selected from SEQ ID NO: 7 or SEQ ID NO: 80.

2. A kit for making an injectable formulation for bone or cartilage repair, the kit comprising:

a first syringe containing an aqueous solution comprising a non-ionic polymer, a gelling agent and a calcium-containing agent; and a vial containing a preparation comprising a synthetic heparin-binding growth factor analog of formula XIII

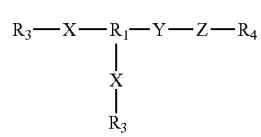

wherein R1 is a diamine amino acid, the diamine amino acid may be an L- or D-diamine amino acid, selected from 2, 3 diamino propionyl amino acid, 2, 4 diamino butylic amino acid, lysine or ornithine;

R3 is a hydrogen (H) such that the terminal group is $NH_2$ or $NH_3^+$;

R4 is $NH_2$, or NH(alkyl);

Y comprises (aminohexanoic acid)$_3$ covalently bonded to $R_1$ and Z;

Z is selected from the group consisting of SEQ ID NO: 2, SEQ ID NO: 3, SEQ ID NO: 4, SEQ ID NO: 5 and SEQ ID NO 6;

X is the same and is selected from SEQ ID NO: 7 or SEQ ID NO: 80.

* * * * *